United States Patent [19]

Rhee et al.

[11] Patent Number: 5,328,955
[45] Date of Patent: Jul. 12, 1994

[54] COLLAGEN-POLYMER CONJUGATES

[75] Inventors: Woonza Rhee, Palo Alto; Donald G. Wallace, Menlo Park, both of Calif.; Alan S. Michaels, Boston, Mass.; Ramon A. Burns, Jr., Fremont, Calif.; Louis Fries, Los Altos, Calif.; Frank DeLustro, Belmont, Calif.; Hanne Bentz, Newark, Calif.

[73] Assignee: Collagen Corporation, Palo Alto, Calif.

[21] Appl. No.: 922,541

[22] Filed: Jul. 30, 1992

Related U.S. Application Data

[63] Continuation-in-part of Ser. No. 433,441, Nov. 14, 1989, Pat. No. 5,162,430, which is a continuation-in-part of Ser. No. 274,071, Nov. 21, 1988, abandoned.

[51] Int. Cl.$^5$ .................... C08G 63/48; A61F 13/00; A61F 2/00
[52] U.S. Cl. .................... 525/54.1; 523/113; 523/115; 424/422; 424/423; 424/426
[58] Field of Search ............ 525/54.1, 937; 523/113, 523/115; 530/356, 840; 424/422, 423, 426

[56] References Cited

U.S. PATENT DOCUMENTS

| | | | |
|---|---|---|---|
| 3,619,371 | 11/1971 | Crook et al. | 525/54.1 |
| 3,788,948 | 1/1974 | Kagedal et al. | 525/54.1 |
| 3,876,501 | 4/1975 | Hanushewsky | 3/1 |
| 3,949,073 | 4/1976 | Daniels et al. | 530/356 |
| 3,960,830 | 6/1976 | Bayer et al. | 530/351 |
| 4,002,531 | 1/1977 | Royer | 435/179 |
| 4,055,635 | 10/1977 | Green et al. | 424/78 |
| 4,088,538 | 5/1978 | Schneider | 435/179 |
| 4,179,337 | 12/1979 | Davis | 525/54.1 |
| 4,192,021 | 3/1980 | Deibig et al. | 3/1.9 |
| 4,261,973 | 4/1981 | Lee et al. | 424/88 |
| 4,301,144 | 11/1981 | Iwashita et al. | 525/54.1 |
| 4,314,380 | 2/1982 | Miyata et al. | 530/356 |
| 4,357,274 | 11/1982 | Werner | 530/350 |
| 4,412,989 | 11/1983 | Iwashita et al. | 525/54.1 |
| 4,414,147 | 11/1983 | Klibanov et al. | 530/356 |
| 4,415,665 | 11/1983 | Mosbach et al. | 435/179 |
| 4,424,208 | 1/1984 | Wallace et al. | 514/21 |

(List continued on next page.)

FOREIGN PATENT DOCUMENTS

| | | |
|---|---|---|
| 098110 | 1/1984 | European Pat. Off. |
| 247860 | 12/1987 | European Pat. Off. |
| 4227265 | 4/1990 | Japan |
| WO84/01106 | 3/1984 | PCT Int'l Appl. |
| WO87/04078 | 7/1987 | PCT Int'l Appl. |

OTHER PUBLICATIONS

Chuapil et al. "Some Chemical and Biological Characteristics of a New Collagen-Polymer Compound Material" J. Biomed Mater. Res. vol. 3, pp. 315-322 (1969).
R. H. L. Chen et al., Properties of Two Urate Oxidases Modified by the Covalent Attachment of Poly(ethylene Glycol), *Biochim Biophys Acta* (1981) 660:293-98.
Davis et al., "Hypouricaemic Effect of Polyethyleneglycol Modified Urate Oxidase," *Lancet* (1981) 2:281-83.

(List continued on next page.)

*Primary Examiner*—Nathan M. Nutter
*Attorney, Agent, or Firm*—Karl Bozicevic

[57] ABSTRACT

Pharmaceutically acceptable, non-immunogenic compositions are formed by covalently binding atelopeptide collagen to pharmaceutically pure, synthetic, hydrophilic polymers via specific types of chemical bonds to provide collagen/polymer conjugates. The atelopeptide collagen can be type I, type II or type III and may be fibrillar or non-fibrillar. The synthetic hydrophilic polymer may be polyethylene glycol and derivatives thereof having a weight average molecular weight over a range of from about 100 to about 20,000. The compositions may include other components such as liquid, pharmaceutically acceptable, carriers to form injectable formulations, and/or biologically active proteins such as growth factors. The collagen-polymer conjugates of the invention generally contain large amounts of water when formed. The conjugates can be dehydrated to form a relatively solid object. The dehydrated, solid object can be ground into particles which can be suspended in a non-aqueous fluid such as an oil and injected into a living being for the purpose of providing soft tissue augmentation. Once in place, the particles rehydrate and expand in size five fold or more.

25 Claims, 2 Drawing Sheets

U.S. PATENT DOCUMENTS

| | | |
|---|---|---|
| 4,451,568 | 5/1984 | Schneider et al. ............... 530/356 |
| 4,488,911 | 12/1984 | Luck et al. ...................... 106/161 |
| 4,495,285 | 1/1985 | Shimizu et al. ................. 435/215 |
| 4,496,689 | 1/1985 | Mitra .............................. 525/54.1 |
| 4,557,764 | 12/1985 | Chu ................................. 106/161 |
| 4,563,350 | 1/1986 | Nathan et al. ..................... 514/21 |
| 4,563,490 | 1/1986 | Stol et al. ....................... 530/356 |
| 4,582,640 | 4/1986 | Smestad et al. ................. 530/356 |
| 4,592,864 | 6/1986 | Miyata et al. ................... 530/356 |
| 4,642,117 | 2/1987 | Nguyen et al. .................... 623/11 |
| 4,678,468 | 7/1987 | Hiroyoshi ........................... 623/11 |
| 4,687,820 | 8/1987 | Hou et al. ...................... 525/54.1 |
| 4,689,399 | 8/1987 | Chu ................................. 530/356 |
| 4,732,863 | 3/1988 | Tomasi et al. ................... 436/547 |
| 4,737,544 | 4/1988 | McCain et al. .................. 424/409 |
| 4,745,180 | 5/1988 | Moreland et al. ................ 530/351 |
| 4,766,106 | 8/1988 | Katre et al. ....................... 524/12 |
| 4,828,563 | 5/1989 | Muller-Lierhern ............... 530/356 |
| 4,847,325 | 7/1989 | Shadle et al. .................. 525/54.1 |
| 4,935,465 | 6/1990 | Garman .......................... 525/54.1 |
| 4,979,959 | 12/1990 | Guire ............................... 530/356 |
| 5,162,430 | 11/1992 | Rhee et al. .................... 525/54.1 |
| 5,201,764 | 4/1993 | Kelman et al. .................. 530/356 |

OTHER PUBLICATIONS

P. S. Pyatak et al., "Preparation of a Polyethylene Glycol: Superoxide Dismutase Adduct, and an Examination of its Blood Circulating Life and Anti-Inflammatory Activity," *Res Com Chem Path Pharmacol* (1980) 29:113-27.

K. J. Wieder et al., "Some Properties of Polyethylene Glycol: Phenylalanine Ammonia-Lyase Adducts," *J Biol Chem* (1979) 254:12579-87.

K. V. Savoca et al., "Preparation of a Non-immunogenic Arginase by the Covalent Attachment of Polyethylene Glycol," *Biochim Biophys Acta* (1979) 578:47-53.

Lloyd et al. "Coupling of acrylic polymer and collagen by use of a water-soluble Carbodimide" *J. Polymer Sci. Chem Ed.* (1979) 17:3473-3483.

A. T. Viau et al. "Safety Evaluation of Free Radical Scavengers PEG-Catalase and PEG-Superoxide Dismutase," *J Free Rad in Bio & Med* (1986) 2:283-288.

A. T. Viau et al. "Toxicologic studies of a conjugate of asparaginase and polyethylene glycol in mice, rats, and dogs," *Am J Vet Res* (1986) 47:1398-401.

Nishida et al., "Hypouricaemic effect after oral administration in chickens of polyethlene glycol-modified uricase entrapped in liposomes," *J Pharm Pharmacol* (1984) 36:354-55.

Inada et al., "Ester Synthesis Catalyzed by Polyethylene Glycol-Modified Lipase in Benzene," *Boichem & Biophys Res Comm* (1984) 122:845-50.

Takahashi et al., "A Chemical Modification to Make Horseradish Peroxidase Soluble and Active in Benzene," *Biochem & Biophys Res Comm* (1984) 121:261-65.

Abuchowski et al., "Cancer Therapy with Chemically Modified Enzymes. I. Antitumor Properties of Polyethylene Glycol-Asparaginase Conjugates," *Cancer Biochem Biophys* (1984) 7:175-86.

J. A. M. Ramshaw et al., "Precipitation of Collagens by Polyethlene Glycols," *Anal Biochem* (1984) 141:361-65.

A. Bendich et al., "Immunological effects of native and polyethylene glycol-modified asparaginases from *Vibrio succinogenes* and *Escherichia coli* in normal and tumour-bearing mice," *Clin Exp Immunol* (1982) 48:273-78.

COLLAGEN-POLYMER CONJUGATES

CROSS-REFERENCES

This application is a continuation-in-part of copending U.S. application Ser. No. 07/433,441 filed Nov. 14, 1989 and now U.S. Pat. No. 5,162,430, which is a continuation-in-part of U.S. patent application Ser. No. 07/274,071, filed Nov. 21, 1988 and now abandoned, both of which are incorporated herein by reference in full and to which applications we claim priority under 35 USC §120.

TECHNICAL FIELD

This invention relates to collagen conjugates and specifically to pharmaceutically acceptable, non-immunogenic, compositions comprising collagen modified by conjugation with synthetic hydrophilic polymers such as polyethylene glycol (PEG) wherein the collagen and PEG are covalently bound via specific linkages such as ether linkages.

BACKGROUND OF THE INVENTION

Collagen is the major protein component of bone, cartilage, skin, and connective tissue in animals. Collagen in its native form is typically a rigid, rod-shaped molecule approximately 300 nm long and 1.5 nm in diameter. It is composed of three collagen polypeptides which form a tight triple helix. The collagen polypeptides are characterized by a long midsection having the repeating sequence —Gly—X—Y—, where X and Y are often proline or hydroxyproline, bounded at each end by the "telopeptide" regions, which constitute less than about 5% of the molecule. The telopeptide regions of the collagen chains are typically responsible for the crosslinking between chains, and for the immunogenicity of the protein. Collagen occurs in several "types", having differing physical properties. The most abundant types are Types I-III.

Collagen is typically isolated from natural sources, such as bovine hide, cartilage, or bones. Bones are usually dried, defatted, crushed, and demineralized to extract collagen, while hide and cartilage are usually minced and digested with proteolytic enzymes (other than collagenase). As collagen is resistant to most proteolytic enzymes, this procedure conveniently serves to remove most of the contaminating protein found with collagen.

Collagen may be denatured by boiling, which produces the familiar product gelatin.

Daniels et al U.S. Pat. No. 3,949,073, disclosed the preparation of soluble collagen by dissolving tissue in aqueous acid, followed by enzymatic digestion. The resulting atelopeptide collagen is soluble, and substantially less immunogenic than unmodified collagen. It may be injected into suitable locations of a subject with a fibril-formation promoter (described as a polymerization promoter in the patent) to form fibrous collagen implants in situ, for augmenting hard or soft tissue. This material is now commercially available from Collagen Corporation (Palo Alto, Calif.) under the trademark Zyderm® collagen implant.

Luck et al U.S. Pat. No. 4,488,911, disclosed a method for preparing collagen in solution (CIS), wherein native collagen is extracted from animal tissue in dilute aqueous acid, followed by digestion with an enzyme such as pepsin, trypsin, or Pronase®. The enzyme digestion removes the telopeptide portions of the collagen molecules, providing "atelopeptide" collagen in solution. The atelopeptide CIS so produced is substantially non-immunogenic, and is also substantially noncross-linked due to loss of the primary crosslinking regions. The CIS may then be precipitated by dialysis in a moderate shear environment to produce collagen fibers which resemble native collagen fibers. The precipitated, reconstituted fibers may additionally be crosslinked using a chemical agent (for example aldehydes such as formaldehyde and glutaraldehyde), or using heat or radiation. The resulting products are suitable for use in medical implants due to their biocompatability and reduced immunogenicity.

Wallace et al U.S. Pat. No. 4,424,208, disclosed an improved collagen formulation suitable for use in soft tissue augmentation. Wallace's formulation comprises reconstituted fibrillar atelopeptide collagen (for example, Zyderm® collagen) in combination with particulate, crosslinked atelopeptide collagen dispersed in an aqueous medium. The addition of particulate crosslinked collagen improves the implant's persistence, or ability to resist shrinkage following implantation.

Smestad et al U.S. Pat. No. 4,582,640, disclosed a glutaraldehyde crosslinked atelopeptide CIS preparation (GAX) suitable for use in medical implants. The collagen is crosslinked under conditions favoring intrafiber bonding rather than interfiber bonding, and provides a product with higher persistence than non-cross-linked atelopeptide collagen, and is commercially available from Collagen Corporation under the trademark Zyplast® Implant.

Nguyen et al U.S. Pat. No. 4,642,117, disclosed a method for reducing the viscosity of atelopeptide CIS by mechanical shearing. Reconstituted collagen fibers are passed through a fine-mesh screen until viscosity is reduced to a practical level for injection.

Nathan et al U.S. Pat. No. 4,563,350, disclosed osteoinductive bone repair compositions comprising an osteoinductive factor, at least 5% nonreconstituted (afibrillar) collagen, and the remainder reconstituted collagen and/or mineral powder (e.g., hydroxyapatite). CIS may be used for the nonreconstituted collagen, and Zyderm® collagen implant (ZCI) is preferred for the reconstituted collagen component. The material is implanted in bone defects or fractures to speed ingrowth of osteoclasts and promote new bone growth.

Chu U.S. Pat. No. 4,557,764, disclosed a "second nucleation" collagen precipitate which exhibits a desirable malleability and putty-like consistency. Collagen is provided in solution (e.g., at 2-4 mg/mL), and a "first nucleation product" is precipitated by rapid titration and centrifugation. The remaining supernatant (containing the bulk of the original collagen) is then decanted and allowed to stand overnight. The precipitated second nucleation product is collected by centrifugation.

Chu U.S. Pat. No. 4,689,399, disclosed a collagen membrane preparation, which is prepared by compressing and drying a collagen gel. The resulting product has high tensile strength.

J. A. M. Ramshaw et al, *Anal Biochem* (1984) 141:361-65, and PCT application WO87/04078 disclosed the precipitation of bovine collagen (types I, II, and III) from aqueous PEG solutions, where there is no binding between collagen and PEG.

Werner U.S. Pat. No. 4,357,274, disclosed a method for improving the durability of sclero protein (e.g., brain meninges) by soaking the degreased tissue in H₂O₂ or PEG for several hours prior to lyophilizing. The resulting modified whole tissue exhibits increased persistence.

Hiroyoshi U.S. Pat. No. 4,678,468, disclosed the preparation of polysiloxane polymers having an interpenetrating network of water-soluble polymer dispersed within. The water-soluble polymer may be a collagen derivative, and the polymer may additionally include heparin. The polymers are shaped into artificial blood vessel grafts, and are designed to prevent clotting.

Other patents disclose the use of collagen preparations with bone fragments or minerals. For example, Miyata et al U.S. Pat. No. 4,314,380 disclosed a bone implant prepared by baking animal bone segments, and soaking the baked segments in a solution of atelopeptide collagen. Deibig et al U.S. Pat. No. 4,192,021 disclosed an implant material which comprises powdered calcium phosphate in a pasty formulation with a biodegradable polymer (which may be collagen). Commonly-owned copending U.S. patent application Ser. No. 855,004, filed Apr. 22, 1986, disclosed a particularly effective bone repair material comprising autologous bone marrow, collagen, and particulate calcium phosphate in a solid, malleable formulation.

There are several references in the art to proteins modified by covalent conjugation to polymers, to alter the solubility, antigenicity and biological clearance of the protein. For example, U.S. Pat. No. 4,261,973 disclosed the conjugation of several allergans to PEG or PPG (polypropylene glycol) to reduce the proteins' immunogenicity. U.S. Pat. No. 4,301,144 disclosed the conjugation of hemoglobin with PEG and other polymers to increase the protein's oxygen carrying capability. EPO 98,110 disclosed coupling an enzyme or interferon to a polyoxyethylene-polyoxypropylene (POE-POP) block polymer increases the protein's halflife in serum. U.S. Pat. No. 4,179,337 disclosed conjugating hydrophilic enzymes and insulin to PEG or PPG reduce immunogenicity. Davis et al, *Lancet* (1981) 2:281–83 disclosed the enzyme uricase modified by conjugation with PEG to provide uric acid metabolism in serum having a long halflife and low immunogenicity. Nishida et al, *J Pharm Pharmacol* (1984) 36.:354–55 disclosed PEG-uricase conjugates administered orally to chickens, demonstrating decreased serum levels of uric acid. Inada et al, *Biochem & Biophys Res Comm* (1984) 122:845–50 disclosed lipoprotein lipase conjugation with PEG to render it soluble in organic solvents. Takahashi et al, *Biochem & Biophys Res Comm* (1984) 121:261–65 disclosed HRP conjugated with PEG to render the enzyme soluble in benzene. Abuchowski et al, *Cancer Biochem Biophys* (1984) 7:175–86 disclosed that enzymes such as asparaginase, catalase, uricase, arginase, trypsin, superoxide dismutase, adenosine deaminase, phenylalanine ammonia-lyase, and the like, conjugated with PEG exhibit longer half-lives in serum and decreased immunogenicity. However, these references are essentially concerned with modifying the solubility and biological characteristics of proteins administered in low concentrations in aqueous solution.

M. Chvapil et al, *J Biomed Mater Res* (1969) 3:315–32 disclosed a composition prepared from collagen sponge and a crosslinked ethylene glycol monomethacrylate-ethylene glycol dimethacrylate hydrogel. The collagen sponge was prepared by lyophilizing an aqueous mixture of bovine hide collagen and methylglyoxal (a tanning agent). The sponge-hydrogel composition was prepared by polymerizing ethylene glycol monomethacrylate and ethylene glycol dimethacrylate in the sponge.

SUMMARY OF THE INVENTION

Pharmaceutically acceptable, non-immunogenic compositions are formed by covalently binding atelopeptide collagen to pharmaceutically pure, synthetic, hydrophilic polymers via specific types of chemical bonds to provide collagen/polymer conjugates. The atelopeptide collagen can be type I, type II or type III and may be fibrillar or non-fibrillar. The synthetic hydrophilic polymer may be polyethylene glycol and derivatives thereof having a weight average molecular weight over a range of from about 100 to about 20,000. The compositions may include other components such as pharmaceutically acceptable fluid carriers to form injectable formulations, and/or biologically active proteins such as cytokines. The collagen-polymer conjugates of the invention generally contain large amounts of water when formed. The conjugates can be dehydrated to form a relatively solid object. The dehydrated, solid object can be ground into particles which can be suspended in a non-aqueous fluid and injected into a living being for the purpose of soft tissue augmentation. Once in place, the particles rehydrate and expand in size five fold or more.

The essence of the invention relates to the collagen/polymer conjugates which are applied and used in a variety of medical and pharmaceutical applications. Although all aspects of the invention generally relate to these conjugates, the invention can be categorized into the following eight different embodiments: (1) the most basic embodiment includes the collagen/polymer conjugates and pharmaceutical compositions which are formulated using these conjugates, which compositions include pharmaceutically acceptable carriers in different types and amounts. (2) One of the most important uses for the conjugates and compositions of the invention is in methods of effecting soft tissue augmentation. The compositions are formulated in a flowable form and injected into patients, such as into facial areas, in order to provide for soft tissue augmentation. The method can be varied so that the reaction between the collagen and the polymer occurs in situ. Furthermore, the conjugates can be dehydrated and then ground into particles, suspended in an inert, non-aqueous carrier, and injected into a patient. After injection, the carrier will be removed by natural physiological conditions and the particles will rehydrate and swell to their original size. (3) All types of conjugates and conjugate compositions of the invention can be combined with various types of cytokines. The cytokines may be either simply admixed with the PEG-collagen conjugate or chemically conjugated to di- or multifunctional PEG-collagen (collagen-PEG-cytokine). In the case of an admixture, the cytokines are not chemically bound to the PEG-collagen and may migrate away from the site of administration into the surrounding tissue providing for sustained release and local therapeutic effects. In the case of the cytokine that is chemically conjugated to the collagen-polymer, the cytokine retains its biological activity even while bound to the conjugate. (4) The various conjugates and compositions of the invention can be further combined with particles and materials in order to increase the structural integrity of the compositions so that they can be used in the augmentation of hard tissue such as bone and cartilage. (5) The conjugates and compositions containing the conjugates can be coated on to various medical devices, including catheters, bone implants, and platinum wires to treat aneurysms. (6) The conjugates can be formulated into various ophthalmic devices, such as lenticules or corneal shields. (7) The reactions between the collagen and the polymer can be designed in a manner so as to form tubular, cylindrical, or spherical shapes for use as nerve growth tubes, blood vessel grafts or breast implant shells. (8) The conjugates and conjugate formulations of the invention can be covalently bound to the chemically derivatized surface of silicon breast implants to prevent capsular contracture and formation of scar tissue.

A primary object of the invention is to provide collagen-polymer conjugates formed by covalently binding polymers such as polyethylene glycol to collagen.

Another object of the invention is to provide pharmaceutically acceptable, non-immunogenic compositions comprising pharmaceutically acceptable liquid carriers having collagen-polymer conjugates therein.

Another object of the invention is to provide a method of tissue augmentation comprising forming the collagen-polymer conjugates, dehydrating the conjugates to form a solid, grinding the solid into particles, suspending the particles in a liquid non-aqueous carrier and injecting the suspension into the site of augmentation after which the particles will rehydrate and expand in size.

An important advantage of the present invention is that the collagen-polymer conjugates have a high degree of stability over long periods of time under physiological conditions.

A feature of the invention is that the conjugates can be formed using a range of different molecular weight polymers in order to adjust physical characteristics of the resulting composition.

Another advantage of the present invention is that the collagen-polymer conjugates have superior handling characteristics as compared with conventional collagen compositions.

Another advantage of the present invention is that the collagen-polymer conjugate compositions generate a decreased immune reaction as compared with conventional pharmaceutically acceptable collagen compositions and collagen compositions crosslinked by other means, such as heat, irradiation, or glutaraldehyde treatment.

Other advantages and features of the present invention is that the collagen-polymer compositions have improved moldability, malleability, and elasticity as compared with conventional collagen compositions.

Other features of the present invention include the ability to formulate the compositions and conjugates in combination with pharmaceutically active molecules such as cytokines in order to improve the activity and available half-life of such cytokines under physiological conditions.

Another feature of the present invention is that the collagen is bound to the polymer by means of a covalent ether linkage.

Another advantage of the present invention is that due to the presence of the ether linkage, the covalent bond between the collagen and the polymer is resistant to breakage due to hydrolysis.

These and other objects, advantages and features of the present invention will become apparent to those persons skilled in the art upon reading the details of the structure, synthesis, and usage of the collagen-polymer conjugates as more fully set forth below, reference being made to the attached figures and included specific examples and formulations forming a part hereof.

DETAILED DESCRIPTION OF PREFERRED EMBODIMENTS OF THE INVENTION

Figure 1:
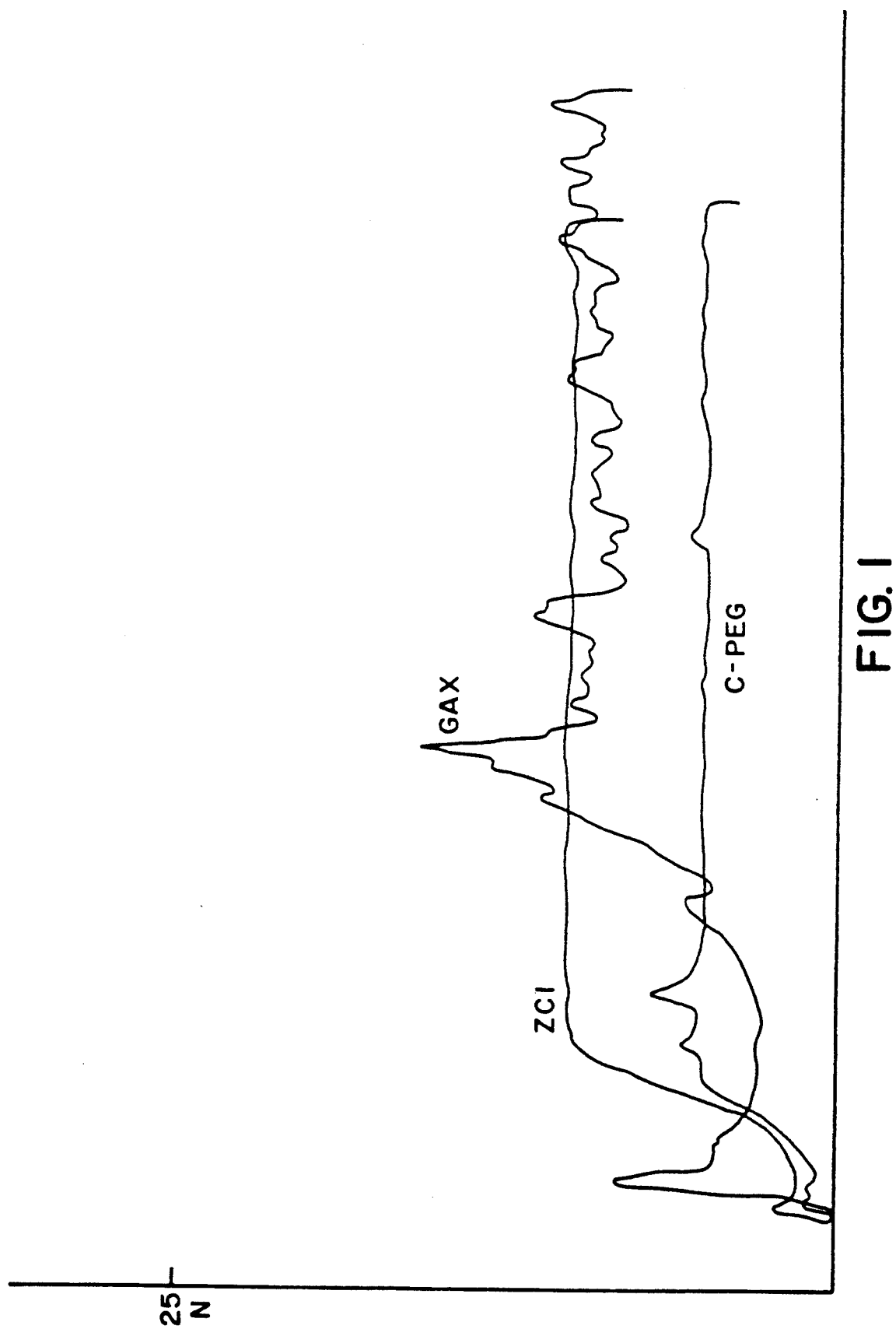
FIG. 1 depicts the force necessary to extrude three compositions: Zyderm® collagen implant (ZCI), a glutaraldehyde-crosslinked collagen (GAX), and a collagen-PEG conjugate of the invention.

Before the present collagen-polymer conjugates and processes for making and using such are described, it is to be understood that this invention is not limited to the particular conjugates or processes and methods described as such may, of course, vary. It is also to be understood that the terminology used herein is for the purpose of describing particular embodiments only, and is not intended to be limiting as the scope of the present invention will be limited only by the appended claims.

It must be noted that, as used in this specification and the appended claims, the singular forms "a", "an" and "the" include plural referrents unless the context clearly dictates otherwise. Thus, for example, reference to "a polymer" includes mixtures of polymers reference to "an amino group" includes one or more different types of amino groups known to those skilled in the art and reference to "the collagen" includes mixtures of different types of collagens and so forth.

Unless defined otherwise, all technical and scientific terms used herein have the same meaning as commonly understood by one of ordinary skill in the art to which this invention belongs. Although any methods and materials similar or equivalent to those described herein may be useful in the practice or testing of the present invention, preferred methods and materials are described below. All publications mentioned herein are incorporated herein by reference. Further, specific terminology of particular importance to the description of the present invention is defined below.

A. DEFINITIONS

The term "collagen" as used herein refers to all forms of collagen, including those which have been processed or otherwise modified. Preferred collagens are treated to remove the immunogenic telopeptide regions ("atelopeptide collagen"), are soluble, and may be in the fibrillar or non-fibrillar form. Type I collagen is best suited to most applications involving bone or cartilage repair. However, other forms of collagen are also useful in the practice of the invention, and are not excluded from consideration here. Collagen crosslinked using heat, radiation, or chemical agents such as glutaraldehyde may be conjugated with polymers as described herein to form particularly rigid compositions. Collagen crosslinked using glutaraldehyde or other (nonpolymer) linking agents is referred to herein as "GAX" while collagen crosslinked using heat and/or radiation is termed "HRX." Collagen used in connection with the preferred embodiments of the invention is in a pharmaceutically pure form such that it can be incorporated into a human body for the intended purpose.

The term "synthetic hydrophilic polymer" as used herein refers to a synthetic polymer having an average molecular weight and composition which renders the polymer essentially water-soluble. Preferred polymers are highly pure or are purified to a highly pure state such that the polymer is or is treated to become pharmaceutically pure. Most hydrophilic polymers can be rendered water-soluble by incorporating a sufficient number of oxygen (or less frequently nitrogen) atoms available for forming hydrogen bonds in aqueous solutions. Preferred polymers are hydrophilic but not soluble. Hydrophilic polymers used herein include polyethylene glycol, polyoxyethylene, polymethylene glycol, polytrimethylene glycols, polyvinylpyrrolidones, and derivatives thereof. The polymers can be linear or multiply branched and will not be substantially crosslinked. Other suitable polymers include polyoxyethylenepolyoxypropylene block polymers and copolymers. Polyoxyethylene-polyoxypropylene block polymers having an ethylene diamine nucleus (and thus having four ends) are also available and may be used in the practice of the invention. Naturally occurring polymers such as proteins, starch, cellulose, heparin, and the like are expressly excluded from the scope of this definition although the invention includes polymer mixtures with naturally occurring polymers therein. All suitable polymers will be non-toxic, non-inflammatory and nonimmunogenic when administered subcutaneously, and will preferably be essentially nondegradable in vivo over a period of at least several months. The hydrophilic polymer may increase the hydrophilicity of the collagen, but does not render it water-soluble. Presently preferred hydrophilic polymers are mono-, di-, and multifunctional polyethylene glycols (PEG). Monofunctional PEG has only one reactive hydroxy group, while difunctional PEG has reactive groups at each end. Monofunctional PEG preferably has a weight average molecular weight between about 100 and about 15,000, more preferably between about 200 and about 8,000, and most preferably about 4,000. Difunctional PEG preferably has a molecular weight of about 400 to about 40,000, more preferably about 3,000 to about 10,000. Multifunctional PEG preferably has a molecular weight between about 3,000 and 100,000.

PEG can be rendered monofunctional by forming an alkylene ether at one end. The alkylene ether may be any suitable alkoxy radical having 1-6 carbon atoms, for example, methoxy, ethoxy, propoxy, 2-propoxy, butoxy, hexyloxy, and the like. Methoxy is presently preferred. Difunctional PEG is provided by allowing a reactive hydroxy group at each end of the linear molecule. The reactive groups are preferably at the ends of the polymer, but may be provided along the length thereof. Polyfunctional molecules are capable of crosslinking the compositions of the invention, and may be used to attach cytokines to collagen.

The term "chemically conjugated" as used herein means attached through a covalent chemical bond. In the practice of the invention, a synthetic hydrophilic polymer and collagen may be chemically conjugated by using a linking radical, so that the polymer and collagen are each bound to the radical, but not directly to each other. The term "collagen-polymer" refers to collagen chemically conjugated to a synthetic hydrophilic polymer, within the meaning of this invention. Thus, "collagen-PEG" (or "PEG-collagen) denotes a composition of the invention wherein collagen is chemically conjugated to PEG. "Collagen-dPEG" refers to collagen chemically conjugated to difunctional PEG, wherein the collagen molecules are typically crosslinked. "Crosslinked collagen" refers to collagen in which collagen molecules are linked by covalent bonds with polyfunctional (including difunctional) polymers. Terms such as "GAX-dPEG" and "HRX-dPEG" indicate collagen crosslinked by both a difunctional hydrophilic polymer and a crosslinking agent such as glutaraldehyde or heat. The polymer may be "chemically conjugated" to the collagen by means of a number of different types of chemical linkages. For example, the conjugation can be via an ester or urethane linkage, but is more preferably by means of an ether linkage. An ether linkage is preferred in that it can be formed without the use of toxic chemicals and is not readily susceptible to hydrolysis in vivo.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weight indicates that the average molecular weight may be any value between the limits specified, and may include molecules outside those limits. Thus, a molecular weight range of about 800 to about 20,000 indicates an average molecular weight of at least about 800, ranging up to about 20 kDa.

The term "available lysine residue" as used herein refers to lysine side chains exposed on the outer surface of collagen molecules, which are positioned in a manner to allow reaction with activated PEG. The number of available lysine residues may be determined by reaction with sodium 2,4,6-trinitrobenzenesulfonate (TNBS).

The terms "treat" and "treatment" as used herein refer to augmentation, repair, prevention, or alleviation of defects, particularly defects due to loss or absence of soft tissue or soft tissue support, or to loss or absence of bone. Additionally, "treat" and "treatment" also refer to the prevention, maintenance, or alleviation of disorders or disease using a biologically active protein coupled to the collagen-polymer composition of the invention. Accordingly, treatment of soft tissue includes augmentation of soft tissue, for example implantation of collagen-polymer conjugates of the invention to restore normal or desirable dermal contours, as in the removal of dermal creases or furrows, or as in the replacement of subcutaneous fat in maxillary areas where the fat is lost due to aging, or in the augmentation of submucosal tissue such as the urinary or lower esophageal sphincters. Treatment of bone and cartilage includes the use of collagen-polymer conjugates, and particularly collagen-PEG in combination with suitable particulate materials, to replace or repair bone tissue, for example, in the treatment of bone nonunions or fractures. Treatment of bone also includes use of cartilaginoid collagen-dPEG compositions, with or without additional bone growth factors. Compositions comprising collagen-polymer with ceramic particles, preferably hydroxyapatite and/or tricalcium phosphate, are particularly useful for the repair of stress-bearing bone due to its high tensile strength.

The term "cytokine" is used to describe biologically active molecules including growth factors and active peptides which aid in healing or regrowth of normal tissue. The function of cytokines is two-fold: 1) they can incite local cells to produce new collagen or tissue, or 2) they can attract cells to the site in need of correction. As such, cytokines serve to encourage "biological anchoring" of the collagen implant within the host tissue. As previously described, the cytokines can either be admixed with the collagen-polymer conjugate or chemically coupled to the conjugate. For example, one 30 may incorporate cytokines such as epidermal growth factor (EGF), transforming growth factor (TGF) alpha, TGF-$\beta$(including any combination of TGF-$\beta$s), TGF-$\beta$1, TGF-$\beta$2, platelet derived growth factor (PDGF-AA, PDGF-AB, PDGF-BB), acidic fibroblast growth factor (FGF), basic FGF, connective tissue activating peptides (CTAP), $\beta$-thromboglobulin, insulin-like growth factors, tumor necrosis factors (TNF), interleukins, colony stimulating factors (CSFs), erythropoietin (EPO), nerve growth factor (NGF), interferons (IFN) bone morphogenic protein (BMP), osteogenic factors, and the like. Incorporation of cytokines, and appropriate combinations of cytokines can facilitate the regrowth and remodeling of the implant into normal bone tissue, or may be used in the treatment of wounds. Furthermore, one may chemically link the cytokines to the collagen-polymer composition by employing a suitable amount of multifunctional polymer molecules during synthesis. The cytokines may then be attached to the free polymer ends by the same method used to attach PEG to collagen, or by any other suitable method. By tethering cytokines to the implant, the effective amount of cytokine is substantially reduced. Dried collagen-PEG compositions having sponge-like characteristics may be prepared as wound dressings, or when incorporated with cytokines, they serve as effective controlled-release drug delivery matrices. By varying the chemical linkage between the collagen and the synthetic polymer, it is possible to vary the effect with respect to the release of the cytokine. For example, when a "ester" linkage is used, the linkage is more easily broken under physiological conditions, allowing for sustained release of the growth factor from the matrix. However, when an "ether" linkage is used, the bonds are not easily broken and the cytokine will remain in place for longer periods of time with its active sites exposed providing a biological effect on the natural substrate for the active site of the protein. It is possible to include a mixture of conjugates with different linkages so as to obtain variations in the effect with respect to the release of the cytokine, i.e., the sustained release effect can be modified to obtain the desired rate of release.

The term "effective amount" refers to the amount of composition required in order to obtain the effect desired. Thus, a "tissue growth-promoting amount" of a composition containing a cytokine refers to the amount of cytokine needed in order to stimulate tissue growth to a detectable degree. Tissue, in this context, includes connective tissue, bone, cartilage, epidermis and dermis, blood, and other tissues. The actual amount which is determined to be an effective amount will vary depending on factors such as the size, condition, sex and age of the patient and can be more readily determined by the caregiver.

The term "sufficient amount" as used herein is applied to the amount of carrier used in combination with the collagen-polymer conjugates of the invention. A sufficient amount is that amount which, when mixed with the conjugate, renders it in the physical form desired, for example, injectable solution, injectable suspension, plastic or malleable implant, rigid stress-bearing implant, and so forth. Injectable formulations generally include an amount of a carrier sufficient to render the composition smoothly injectable without significant need to interrupt the injection process, whereas malleable implants contain substantially less carrier and have a clay-like consistency. Rigid stress-bearing implants may include no carrier at all and have a high degree of structural integrity. The amount of the carrier can be varied and adjusted depending on the particular conjugate used and the end result desired. Such adjustments will be apparent to those skilled in the art.

The term "suitable particulate material" as used herein refers to a particulate material which is substantially insoluble in water, non-immunogenic, biocompatible, and immiscible with collagen-polymer conjugate. The particles of material may be fibrillar, or may range in size from about 20 to 250 $\mu$m in diameter and be bead-like or irregular in shape. Exemplary particulate materials include without limitation fibrillar crosslinked collagen, gelatin beads, crosslinked collagen-dPEG particles, polytetrafluoroethylene beads, silicone rubber beads, hydrogel beads, silicon carbide beads, and glass beads. Preferred particulate materials are calcium phosphates, most preferably, hydroxyapatite and/or tricalcium phosphate.

The term "solid implant" refers to any solid object which is designed for insertion and use within the body, and includes bone and cartilage implants (e.g., artificial joints, retaining pins, cranial plates, and the like, of metal, plastic and/or other materials), breast implants (e.g., silicone gel envelopes, foam forms, and the like), catheters and cannulas intended for long-term use (beyond about three days) in place, artificial organs and vessels (e.g., artificial hearts, pancreases, kidneys, blood vessels, and the like), drug delivery devices (including monolithic implants, pumps and controlled release devices such as Alzet® minipumps, steroid pellets for anabolic growth or contraception, and the like), sutures for dermal or internal use, periodontal membranes, ophthalmic shields, corneal lenticules, and the like.

The term "suitable fibrous material" as used herein, refers to a fibrous material which is substantially insoluble in water, non-immunogenic, biocompatible, and immiscible with the collagen/polymer conjugate of the invention. The fibrous material may comprise a variety of materials having these characteristics and are combined with compositions of the collagen/polymer conjugate in order to form and/or provide structural integrity to various implants or devices used in connection with medical and pharmaceutical uses. For example, the collagen/polymer conjugate compositions of the invention can be coated on the "suitable fibrous material" which can then be wrapped around a bone to provide structural integrity to the bone. Thus, the "suitable fibrous material" is useful in forming the "solid implants" of the invention.

The term "in situ" as used herein means at the site of administration. Thus, the injectable reaction mixture compositions are injected or otherwise applied to a site in need of augmentation, and allowed to crosslink at the site of injection. Suitable sites will generally be intradermal or subcutaneous regions for augmenting dermal support, at the site of bone fractures for wound healing and bone repair, and within sphincter tissue for sphincter augmentation (e.g., for restoration of continence).

The term "aqueous mixture" of collagen includes liquid solutions, suspensions, dispersions, colloids, and the like containing collagen and water.

The term "NFC cartilage" as used herein refers to a composition of the invention which resembles cartilage in physical consistency. NFC cartilage is prepared from nonfibrillar collagen (e.g., collagen in solution) and is crosslinked with a hydrophilic polymer, especially using dPEG. As an artifact of the production process or by design, NFC cartilage may contain about 0-20% fibrillar collagen. NFC cartilage is generally prepared by adding dPEG in acidic solution to an acidic solution of collagen, and allowing conjugation to occur prior to neutralization. The term "NFC-FC cartilage" refers to a composition similar to NFC cartilage, wherein the percentage of fibrillar collagen is about 20-80%. NFC-FC cartilage is generally prepared by adding dPEG in a neutralizing buffer to an acidic solution of collagen. The neutralizing buffer causes collagen fibril formation during the conjugation process. Similarly, "FC cartilage" refers to a composition of the invention which is prepared from fibrillar collagen and a difunctional hydrophilic polymer. FC cartilage may generally be prepared using dPEG and fibrillar collagen in neutral solutions/suspensions.

B. GENERAL METHOD

B.1 Preparation

To form the conjugates of the invention collagen must be chemically bound to a synthetic hydrophilic polymer. This can be carried out in a variety of ways. In accordance with the preferred method, the synthetic hydrophilic polymer is activated and then reacted with the collagen. Alternatively, the hydroxyl or amino groups present on the collagen can be activated and the activated groups will react with the polymer to form the conjugate. In accordance with a less preferred method, a linking group with activated hydroxyl or amino groups thereon can be combined with the polymer and collagen in a manner so as to concurrently react with both the polymer and collagen forming the conjugate. Other methods of forming the conjugates will become apparent to those skilled in the art upon reading this disclosure. Since the conjugates of the invention are to be used in the human body it is important that all of the components, including the polymer, collagen, and linking group, if used form a conjugate that is unlikely to be rejected by the body. Accordingly, toxic and/or immunoreactive components are not preferred as starting materials. Some preferred starting materials and methods of forming conjugates are described further below.

Although different hydrophilic synthetic polymers can be used in connection with forming the conjugate must be biocompatible, relatively insoluble, but hydrophilic and is preferrably one or more forms of polyethylene glycol (PEG), due to its known biocompatiblility. Various forms of PEG are extensively used in the modification of biologically active molecules because PEG can be formulated to have a wide range of solubilities and because it lacks toxicity, antigenicity, immunogenicity, and does not typically interfere with the enzymatic activities and/or conformations of peptides. Further, PEG is generally non-biodegradable and is easily excreted from most living organisms including humans.

The first step in forming the collagen-polymer conjugates of the invention generally involves the functionalization of the PEG molecule. Various functionalized polyethylene glycols have been used effectively in fields such as protein modification (see Abuchowski et al., *Enzymes as Drugs,* John Wiley & Sons: New York, N.Y. (1981) pp. 367-383; and Dreborg et al., *Crit. Rev. Therap. Drug Carrier Syst.* (1990) 6:315, both of which are incorporated herein by reference), peptide chemistry (see Mutter et al., *The Peptides,* Academic: New York, N.Y. 2:285-332; and Zalipsky et al., *Int. J. Peptide Protein Res.* (1987) 30:740, both of which are incorporated herein by reference), and the synthesis of polymeric drugs (see Zalipsky et al., *Eur. Polym. J.* (1983) 19:1177; and Ouchi et al., *J. Macromol. Sci. -Chem.* (1987) A24:1011, both of which are incorporated herein by reference). Various types of conjugates formed by the binding of polyethylene glycol with specific pharmaceutically active proteins have been disclosed and found to have useful medical applications in part due to the stability of such conjugates with respect to proteolytic digestion, reduced immunogenicity and longer half-lives within living organisms.

One form of polyethylene glycol which has been found to be particularly useful is monomethoxypolyethylene glycol (mPEG), which can be activated by the addition of a compound such as cyanuric chloride, then coupled to a protein (see Abuchowski et al., *J. Biol. Chem.* (1977) 252:3578, which is incorporated herein by reference). Although such methods of activating polyethylene glycol can be used in connection with the present invention, they are not particularly desirable in that the cyanuric chloride is relatively toxic and must be completely removed from any resulting product in order to provide a pharmaceutically acceptable composition.

Activated forms of PEG can be made from reactants which can be purchased commercially. One form of activated PEG which has been found to be particularly useful in connection with the present invention is mPEG-succinate-N-hydroxysuccinimide ester (SS-PEG) (see Abuchowski et al., *Cancer Biochem. Biphys,* (1984) 7:175, which is incorporated herein by reference). Activated forms of PEG such as SS-PEG react with the proteins under relatively mild conditions and produce conjugates without destroying the specific biological activity and specificity of the protein attached to the PEG. However, when such activated PEGs are reacted with proteins, they react and form linkages by means of ester bonds. Although ester linkages can be used in connection with the present invention, they are not particularly preferred in that they undergo hydrolysis when subjected to physiological conditions over extended periods of time (see Dreborg et al., *Crit. Rev. Therap. Drug Carrier Syst.* (1990) 6:315; and Ulbrich et al., *J. Makromol. Chem.* (1986) 187:1131, both of which are incorporated herein by reference).

It is possible to link PEG to proteins via urethane linkages, thereby providing a more stable attachment which is more resistant to hydrolytic digestion than the ester linkages (see Zalipsky et al., Polymeric Drug and Drug Delivery Systems, Chapter 10, "Succinimidyl Carbonates of Polyethylene Glycol" (1991) incorporated herein by reference to disclose the chemistry involved in linking various forms of PEG to specific biologically active proteins). The stability of urethane linkages has been demonstrated under physiological conditions (see Veronese et al., *Appl. Biochem. Biotech-* nol. (1985) 11:141; and Larwood et al., *J. Labelled Compounds Radiopharm.* (1984) 21:603, both of which are incorporated herein by reference). Another means of attaching the PEG to a protein can be by means of a carbamate linkage (see Beauchamp et al., *Anal. Biochem.* (1983) 131:25; and Berger et al., *Blood* (1988) 71:1641, both of which are incorporated herein by reference). The carbamate linkage is created by the use of carbonyldiimidazole-activated PEG. Although such linkages have advantages, the reactions are relatively slow and may take 2 to 3 days to complete.

The various means of activating PEG described above and publications (all of which are incorporated herein by reference) cited in connection with the activation means are described in connection with linking the PEG to specific biologically active proteins and not collagen. However, the present invention now discloses that such activated PEG compounds can be used in connection with the formation of collagen-PEG conjugates. Such conjugates provide a range of improved unexpected characteristics and as such can be used to form the various compositions of the present invention. [*Polymeric Drug and Drug Delivery Systems*, Chapter 10, "Succinimidyl Carbonates of Polyethylene Glycol" (1991), incorporated herein by reference to disclose the chemistry involved in linking various forms of PEG to specific biologically active proteins.]

B.2 Specific Forms of Activated PEG

As indicated above, the conjugates of the present invention can be prepared by covalently binding a variety of different types of synthetic hydrophilic polymers to collagen. However, because the final product or conjugate obtained must have a number of required characteristics such as being biocompatible and nonimmunogenic, it has been found useful to use polyethylene glycol as the synthetic hydrophilic polymer. The polyethylene glycol must be modified in order to provide activated groups on one or preferably both ends of the molecule so that covalent binding can occur between the PEG and the collagen. Some specific functionalized forms of PEG are shown structurally below, as are the products obtained by reacting these functionalized forms of PEG with collagen.

The first functionalized PEG is difunctionalized PEG succinimidyl glutarate, referred to herein as (SG-PEG). The structural formula of this molecule and the reaction product obtained by reacting it with collagen is shown below:

FORMULA 1
S-PEG: Difunctional PEG Succinimidyl Glutarate

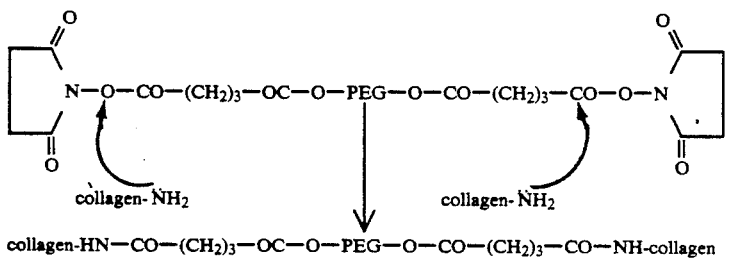

collagen-HN—CO—(CH$_2$)$_3$—OC—O—PEG—O—CO—(CH$_2$)$_3$—CO—NH-collagen

Another difunctionally activated form of PEG is referred to as PEG succinimidyl (S-PEG). The structural formula for this compound and the reaction product obtained by reacting it with collagen is shown below. It should be noted that the methyl group is re-peated twice. In a general structural formula for this compound, the 2 is replace with an "n" and in this embodiment, n=3, in that there are three repeating CH$_8$2 groups on each side of the PEG. The above structure results in a conjugate which includes a "ether" linkage which is not subject to hydrolysis. This is distinct from the first conjugate shown above, wherein an ester linkage is provided. The ester linkage is subject to hydrolysis under physiological conditions.

FORMULA 2
S-PEG, n = 3: Difunctional PEG Succinimidyl

N—O—OC—(CH$_2$)$_3$O—PEG—O—(CH$_2$)$_3$CO—O—N collagen-NH$_2$   collagen-NH$_2$ collagen-HN—OC—(CH$_2$)$_3$O—PEG—O—(CH$_2$)$_3$CO—NH-collagen Yet another derivatized form of polyethylene glycol, wherein n=2 is shown below, as is the conjugate formed by reacting the derivatized PEG with collagen.

FORMULA 3
S-PEG, n = 2: Difunctional PEG Succinimidyl

N—O—OC—(CH$_2$)$_2$O—PEG—O—(CH$_2$)$_2$CO—O—N collagen-NH$_2$   collagen-NH$_2$ collagen-HN—OC—(CH$_2$)$_2$O—PEG—O—(CH$_2$)$_2$CO—NH-collagen In another preferred embodiment of the invention similar to the immediate two above formulas, is provided when n=1. The structural formula and resulting conjugate are shown below. It is noted that the conjugate includes both an ether and a peptide linkage. These linkages are stable under physiological conditions.

FORMULA 4
S-PEG, n = 1: Difunctional PEG Succinimidyl

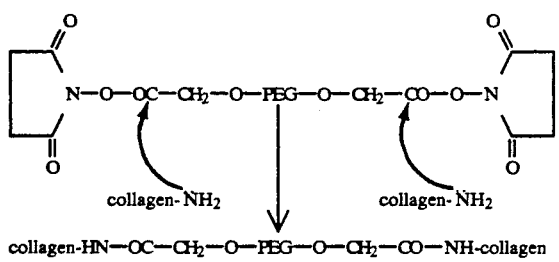

FORMULA 6
A-PEG: Difunctional PEG Propion Aldehyde

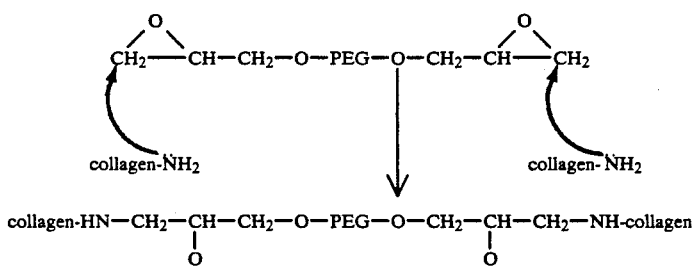

Yet another functionalized form of polyethylene glycol is difunctional PEG glycidyl ether (E-PEG), which is shown below, as is the conjugate formed by reacting such with collagen.

FORMULA 7
E-PEG: Difunctional PEG Glycidyl Ether $$\text{CH}_2\overset{O}{\underset{}{\diagdown\diagup}}\text{CH}-\text{CH}_2-\text{O}-\text{PEG}-\text{O}-\text{CH}_2-\text{CH}\overset{O}{\underset{}{\diagdown\diagup}}\text{CH}_2$$

collagen-$NH_2$      collagen-$NH_2$ collagen-HN—$CH_2$—CH—$CH_2$—O—PEG—O—$CH_2$—CH—$CH_2$—NH-collagen
                                O                            O Yet another derivatized form of PEG is provided when n=0. The difunctionalized form is referred to as PEG succinimidyl carbonate (SC-PEG). The structural formula of this compound and the conjugate formed by reacting SC-PEG with collagen is shown below. Although this conjugate includes a urethane linkage, the conjugate has been found not to have a high degree of stability under physiological conditions.

FORMULA 5
SC-PEG, n = 0: Difuntional PEG Succinimidyl Carbonate

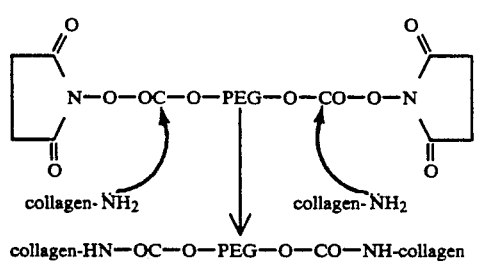

All of the above derivatives involve the inclusion of the succinimidyl group. However, different activating groups can be attached to one or both ends of the PEG. For example, the PEG can be derivatized to form difunctional PEG propion aldehyde (A-PEG), which is shown below, as is the conjugate formed by the reaction of A-PEG with collagen.

FORMULA 6
A-PEG: Difunctional PEG Propion Aldehyde

The conjugates formed using the functionalized forms of PEG vary depending on the functionalized form of PEG which is used in the reaction. Furthermore, the final product can be varied with respect to its characteristics by changing the molecular weight of the PEG. In general, the stability of the conjugate is improved by eliminating any ester linkages between the PEG and the collagen and including ether and/or urethane linkages. In certain situations, it is desirable to include the weaker ester linkages so that the linkages are gradually broken by hydrolysis under physiological conditions, breaking apart the matrix and releasing a component held therein, such as a growth factor. By varying the chemical structure of the linkage, the rate of sustained release can be varied.

The crosslinking reaction between the collagen and polymer may be performed in vitro, or a reaction mixture may be injected for crosslinking in situ. At sufficient density, crosslinked collagen-polymer conjugates resemble cartilage, and are useful as substitutes thereof, (e.g., cranial onlay, ear and nose reconstruction, and the like). Polyfunctional polymers may also be used to crosslink collagen molecules to other proteins (e.g., glycosaminoglycans, chondroitin sulfates, fibronectin, and the like), particularly growth factors, for compositions particularly suited for use in wound healing, osteogenesis, and immune modulation. Such tethering of cytokines to collagen molecules provides an effective slow-release drug delivery system.

Suitable collagens include all types of collagen, preferably types I, II and III. Collagens may be soluble (for example, commercially available Vitrogen ® 100 collagen-in-solution), and may or may not have the telopeptide regions. Preferably, the collagen will be reconstituted fibrillar atelopeptide collagen, for example Zyderm ® collagen implant (ZCI) or atelopeptide collagen in solution (CIS). Various forms of collagen are available commercially, or may be prepared by the processes described in, for example, U.S. Pat. Nos. 3,949,073; 4,488,911; 4,424,208; 4,582,640; 4,642,117; 4,557,764; and 4,689,399, all incorporated herein by reference. Non-fibrillar, atelopeptide, reconstituted collagen is preferred in order to form certain products.

The compositions of the invention comprise collagen chemically conjugated to a selected synthetic hydrophilic polymer or polymers. Collagen contains a number of available amino and hydroxy groups which may be used to bind the synthetic hydrophilic polymer. The polymer may be bound using a "linking group", as the native hydroxy or amino groups in collagen and in the polymer frequently require activation before they can be linked. For example, one may employ compounds such as dicarboxylic anhydrides (e.g., glutaric or succinic anhydride) to form a polymer derivative (e.g., succinate), which may then be activated by esterification with a convenient leaving group, for example, N-hydroxysuccinimide, N,N'-disuccinimidyl oxalate, N,N'-disuccinimidyl carbonate, and the like. See also Davis, U.S. Pat. No. 4,179,337 for additional linking groups. Presently preferred dicarboxylic anhydrides that are used to form polymer-glutarate compositions include glutaric anhydride, adipic anhydride, 1,8-naphthalene dicarboxylic anhydride, and 1,4,5,8-naphthalenetetracarboxylic dianhydride. The polymer thus activated is then allowed to react with the collagen, forming a collagen-polymer composition of the invention.

CONJUGATES WITH ESTER LINKAGES

In one embodiment, a pharmaceutically pure form of monomethylpolyethylene glycol (mPEG) (mw 5,000) is reacted with glutaric anhydride (pure form) to create mPEG glutarate. The glutarate derivative is then reacted with N-hydroxysuccinimide to form a succinimidyl monomethylpolyethylene glycol glutarate. The succinimidyl ester (mPEG*, denoting the activated PEG intermediate) is then capable of reacting with free amino groups present on collagen (lysine residues) to form a collagen-PEG conjugate of the invention wherein one end of the PEG molecule is free or non-bound. Other polymers may be substituted for the monomethyl PEG, as described above. Similarly, the coupling reaction may be carried out using any known method for derivatizing proteins and synthetic polymers. The number of available lysines conjugated may vary from a single residue to 100% of the lysines, preferably 10-50%, and more preferably 20-30%. The number of reactive lysine residues may be determined by standard methods, for example by reaction with TNBS.

The resulting product is a smooth, pliable, rubbery mass having a shiny appearance. It may be wetted, but is not water-soluble. It may be formulated as a suspension at any convenient concentration, preferably about 30-65 mg/mL, and may be implanted by injection through a suitable syringe. The consistency of the formulation may be adjusted by varying the amount of liquid used.

COMPOSITIONS FOR BONE REPAIR

Formulations suitable for repair of bone defects or nonunions may be prepared by providing high concentration compositions of collagen-polymer, or by admixture with suitable particulate materials. When making bone repair compositions, the linkage between the collagen and polymer must be an ether linkage in order to avoid deterioration due to the hydrolysis of the ester linkages. Such collagen-polymer particulate compositions may be malleable or rigid, depending on the amount of liquid incorporated. Formulations for treatment of stress-bearing bone are preferably dried and rigid, and will generally comprise between about 45% and 85% particulate mineral, for example hydroxyapatite, tricalcium phosphate, or mixtures thereof. The tensile strength and rigidity may be further increased by heating the composition under vacuum at about 60°-90° C., preferably about 75° C., for about 5 to 15 hours, preferably about 10 hours. Malleable compositions may be used for repair of non-stressed bone or cartilage.

The activated mPEG, may be replaced, in whole or in part, by difunctional activated PEG (dPEG*, e.g., non-methylated PEG which is then activated at each end), thus providing a crosslinked or partially crosslinked collagen composition. Such compositions are, however, quite distinct from conventionally-crosslinked collagen compositions (e.g., using heat, radiation, glutaraldehyde, and the like), as the long-chain synthetic hydrophilic polymer imparts a substantial hydrophilic character to the composition. In a presently preferred embodiment, approximately 1-20% of the mPEG is difunctional PEG. The character of the composition may be adjusted as desired, by varying the amount of difunctional PEG included during the process.

In another presently preferred embodiment, difunctional PEG* (substantially 100% at pH 7) is used to crosslink collagen. In one version, CIS (about 3-100 mg/mL, preferably about 10-40 mg/mL) is allowed to react with dPEG* (difunctional PEG activated at each end by addition of an acid anhydride having a leaving group such as succinimide) having a molecular weight of about 2,000 to about 20,000 (preferably about 3,400-10,000) which is added as a concentrated solution to a final reaction mixture concentration of about 5-40%, preferably about 10-20%. This represents a 5- to 10-fold excess of dPEG* to collagen on a molar basis. The collagen molecules bind to dPEG*, without mechanical mixing or agitation, and settle out of solution to produce a cartilaginoid collagen-polymer conjugate containing approximately 20-80% fibrillar collagen. The conjugate is then washed with PBS to remove any remaining unreacted dPEG,, providing the material of the invention. A cartilaginoid collagen-polymer conjugate may also be prepared by mixing dPEG* solution (pH 3) with collagen-in-solution between two syringes to homogeneity, and then casting into a suitable container (e.g., a Petri dish). A 20% w/v dPEG* solution (pH 7) is then added to the non-fibrillar collagen-PEG solution to result in a lightly cartilaginoid fibrillar collagen-polymer conjugate. The resulting NFC-F conjugate cartilage contains approximately 1-40% fibrillar collagen. The characteristics of the final product may be adjusted by varying the initial reaction conditions. In general, increased collagen and/or polymer concentrations provide a denser, less porous product. By varying the pH of the collagen solution and the dPEG* solution, compositions may be producing over a wide range of fibrillar content. If desired, the denser formulations may be cast or molded into any shape desired, for example into sheets or membranes, into tubes or cylinders, into cords or ropes, and the like.

BREAST IMPLANTS

Collagen-polymer conjugates can also be used as coatings for breast implants. The surface of a standard silicone-shell implant can be chemically derivatized to provide active binding sites for di- or multifunctional PEG-collagen (collagen-PEG-silicone). The presence of the collagen coating bound directly to the silicone via PEG will serve to reduce scar tissue formation and capsular contracture. Unlike typical coated breast implants, scar tissue will not be able to grow between the collagen coating and the surface of the implant itself.

Alternatively, PEG-collagen can be formed into a hollow sphere for use as a breast implant shell. The shell can then be filled with a radiolucent material, such as triglycerides, to facilitate mammography.

COATED MEDICAL DEVICES

The injectable formulations (gels or solutions) may be used to coat implants, catheters, tubes (e.g., for blood vessel replacement), meshes (e.g., for tissue reinforcement), and the like. PEG-collagen formulations can also be used to coat platinum wires, which can then be administered to the site of an aneurysm via catheter. Gels may be prepared by reducing the polymer concentration or reducing the reaction time. CIS is the preferred starting material where the desired properties are high density, rigidity, viscosity, and translucence. However, one may substitute fibrillar collagen (preferably atelopeptide fibrillar collagen such as ZCI) and obtain products which are more opaque, more flexible, and more susceptible to colonization by cells after implantation. CIS-based materials are presently preferred for coating articles to be implanted, such as catheters and stress-bearing bone implants.

CONJUGATE AND CYTOKINES

Compositions of the invention containing cytokines such as EGF and TGF-$\beta$ are prepared by mixing an appropriate amount of the cytokine into the composition, or by incorporating the cytokine into the collagen prior to treatment with activated PEG. By employing an appropriate amount of difunctional PEG, a degree of crosslinking may be established, along with molecules consisting of collagen linked to a cytokine by a synthetic hydrophilic polymer. Preferably, the cytokine is first reacted with a molar excess of dPEG* in a dilute solution over a 3 to 4 hour period. The cytokine is preferably provided at a concentration of about 1 $\mu$g/mL to about 5 mg/mL, while the dPEG* is preferably added to a final concentration providing a 30 to 50-fold molar excess. The resulting conjugated cytokine is then added to an aqueous collagen mixture (about 1 to about 60 mg/mL) at pH 7-8 and allowed to react further. The resulting composition is allowed to stand overnight at ambient temperature. The pellet is collected by centrifugation, and is washed with PBS by vigorous vortexing in order to remove non-bound cytokine.

MEMBRANOUS FORMS

Flexible sheets or membranous forms of the collagen-polymer conjugate may be prepared by methods known in the art, for example, U.S. Pat. Nos. 4,600,533; 4,412,947; and 4,242,291. Briefly, high concentration (10-100 mg/mL) CIS or fibrillar collagen (preferably atelopeptide fibrillar collagen, such as ZCI) is cast into a flat sheet container. A solution of mPEG* (having a molecular weight of approximately 5,000) is added to the cast collagen solution, and allowed to react overnight at room temperature. The resulting collagen-polymer conjugate is removed from the reaction solution using a sterile spatula or the like, and washed with PBS to remove excess unreacted mPEG*.

The resulting conjugate may then be compressed under constant pressure to form a uniform, flat sheet or mat, which is then dried to form a membranous implant of the invention. More flexible membranous forms are achieved by using lower collagen concentrations and high polymer concentrations as starting materials.

Less flexible membranous forms are prepared by using a dPEG* solution rather than mPEG*. CIS, at room temperature, is mixed with a buffer solution and incubated at 37° C. overnight. The resulting gel is compressed under constant pressure, dried, and desalted by washing. The resultant membrane is then crosslinked by treating with dPEG*, washed, and then dried at low temperature.

Alternatively, CIS or fibrillar collagen (10-100 mg/mL) is cast into a flat sheet container. A solution of dPEG* (22-50% w/v) is added to the cast collagen. The mixture is allowed to react over several hours at room temperature. Shorter reaction times result in more flexible membranes. The resulting collagen-polymer membrane may be optionally dehydrated under a vacuum oven, lyophilization, or air-drying.

SPONGES

Collagen-polymer conjugates may also be prepared in the form of sponges, by lyophilizing an aqueous slurry of the composition after conjugation.

B.2 Use and Administration

Compositions of the invention have a variety of uses. Malleable, plastic compositions may be prepared as injectable formulations, and are suitable for dermal augmentation, for example for filling in dermal creases, and providing support for skin surfaces. Such compositions are also useful for augmenting sphincter tissue, (e.g., for restoration of continence). In such cases, the formulation may be injected directly into the sphincter tissue to increase bulk and permit the occluding tissues to meet more easily and efficiently. These compositions may be homogeneous, or may be prepared as suspensions of small microgel collagen-polymer conjugate particles or beads which are delivered in a non-aqueous carrier. The beads/particles rehydrate and swell in situ. This has the advantage over commercial preparations in that less volume of product is required to achieve the desired correction.

Surprisingly, one may administer the reaction mixture by injection before crosslinking has completed. In this embodiment, an aqueous collagen mixture is combined with a low-concentration dPEG, solution, mixed, and the combination injected or applied before the viscosity increases sufficiently to render injection difficult (usually about 20 minutes). Mixing may be accomplished by passing the mixture between two syringes equipped with Luer lock hubs, or through a single syringe having dual compartments (e.g., double barrel). The composition crosslinks in situ, and may additionally crosslink to the endogenous tissue, anchoring the implant in place. In this method, one can use collagen (preferably fibrillar collagen) at a concentration of about 10-100 mg/mL, although abut 30-80 mg/mL is preferred, most preferably about 33 mg/mL. The dPEG* concentration is preferably set at about 0.1 to about 3%, although concentrations as high as 30% may be used if desired. The mixture is injected directly into the site in need of augmentation, and causes essentially no detectable inflammation or foreign body reaction. One may additionally include particulate materials in the collagen reaction mixture, for example hydrogel or collagen-dPEG beads, or hydroxyapatite/tricalcium phosphate particles, to provide a bulkier or more rigid implant after crosslinking.

Compositions of the invention (particularly crosslinked collagen compositions) are also useful for coating articles for implantation or relatively long term residence within the body. Such surface treatment renders the object non-immunogenic, and reduces the incidence of foreign body reactions. Accordingly, one can apply compositions of the invention to catheters, cannulas, bone prostheses, cartilage replacement, breast implants, minipumps and other drug delivery devices, artificial organs, and the like. Application may be accomplished by dipping the object into the reaction mixture while crosslinking is occurring, and allowing the adherent viscous coating to dry. One may pour or otherwise apply the reaction mixture if dipping is not convenient. Alternatively, one may use flexible sheets or membranous forms of collagen-polymer conjugate to wrap the object with, sealing corners and edges with reaction mixture.

In another embodiment, the object may be dipped in a viscous collagen-in-solution bath, or in a fibrillar collagen solution until the object is completely coated. The collagen solution is fixed to the object by dipping the collagen-coated object into a dPEG* (pH 7) solution bath, and then allowing the collagen-polymer coated object to dry. Alternatively, viscous collagen-in-solution is mixed with a dPEG* (pH 3) solution and polymerized rapidly, as described above. The object is dipped in the acidic collagen-polymer solution, and cured by dipping the coated object into a neutralizing buffer containing about 20% by weight dPEG* (pH 7), to result in a collagen-polymer coated object.

Compositions of the invention may be prepared in a form that is dense and rigid enough to substitute for cartilage. These compositions are useful for repairing and supporting tissue which require some degree of structure, for example in reconstruction of the nose, ear, knee, larynx, tracheal rings, and joint surfaces. One can also replace tendon, ligament and blood vessel tissue using appropriately formed cartilaginoid material. In these applications, the material is generally cast or molded into shape: in the case of tendons and ligaments, it may be preferable to form filaments for weaving into cords or ropes. In the case of artificial blood vessels it may be advantageous to incorporate a reinforcing mesh (e.g., nylon or the like).

Compositions of the invention containing cytokines are particularly suited for sustained administration of cytokines, as in the case of wound healing promotion. Osteoinductive factors and cofactors (including TGF-$\beta$) may advantageously be incorporated into compositions destined for bone replacement, augmentation, and/or defect repair. Compositions provided in the form of a membrane may be used to wrap or coat transplanted organs, to suppress rejection and induce improved tissue growth. Similarly, one may coat organs for transplantation using a crosslinking reaction mixture of factor-polymer conjugates and collagen. Alternatively, one may administer antiviral and antitumor factors such as TNF, interferons, CSFs, TGF-$\beta$, and the like for their pharmaceutical activities. The amount of composition used will depend upon the severity of the condition being treated, the amount of factor incorporated in the composition, the rate of delivery desired, and the like. However, these parameters may easily be determined by routine experimentation, for example by preparing a model composition following the examples below, and assaying the release rate in a suitable animal model.

EXAMPLES

The following examples are put forth so as to provide those of ordinary skill in the art with a complete disclosure and description of how to make the conjugates and formulations and implants containing such conjugates and are not intended to limit the scope of what the inventors regard as their invention. Efforts have been made to ensure accuracy with respect to numbers used (e.g. amounts, temperature, molecular weight, etc.) but some experimental errors and deviation should be accounted for. Unless indicated otherwise, parts are parts by weight, molecular weight is weight average molecular weight, temperature is in degrees Centigrade, and pressure is at or near atmospheric.

EXAMPLE 1

Preparation of Collagen-PEG (A) Monomethyl-PEG 5000 (50 g, 10 mmol, Aldrich Chemical Co.) is dissolved in 1,2-dichoroethane (250 mL) and heated at reflux with glutaric anhydride (5 g) and pyridine (4 mL) under nitrogen for 3 days. The solution is then filtered and the solvent evaporated, and the residue dissolved in water (100 mL) and washed with diethyl ether (2×50 mL). The resulting PEG-glutarate is extracted from the water with chloroform (2×50 mL), and the chloroform evaporated to yield about 43 g of PEG-glutarate. The PEG-glutarate is then dissolved in dimethylformamide (DMF, 200 mL) at 37° C., and N-hydroxysuccinimide (10% molar xs) added. The solution is cooled to 0° C. and an equivalent amount of dicyclohexylcarbodiimide added in DMF solution (10 mL). The mixture is left at room temperature for 24 hours, and then filtered. Cold benzene (100 mL) is then added, and the PEG-succinimidyl glutarate (PEG-SG) precipitated by adding petroleum ether (200 mL) at 0° C. The precipitate is collected on a sintered glass filter. Dissolution in benzene, followed by precipitation with petroleum ether is repeated three times to provide "activated" PEG (PEG-SG).

Vitrogen 100 ® collagen in solution (400 mL, 1.2 g collagen, 0.004 mmol) was mixed with 0.2M phosphate buffer (44 mL) to elevate the pH to 7.4. Next, a three-fold molar excess of PEG-SG (6.00 g, 1.2 mmol) was dissolved in water for injection (40 mL) and sterile-filtered. The PEG-SG solution was then added to the collagen solution, and the mixture allowed to stand at 17°–22° C. for about 15 hours. The solution was then centrifuged, and the resulting pellet (25 g) of reconstituted fibrils collected and washed with phosphate-buffered saline (PBS, 3×400 mL) to remove residual PEG. The resulting material has a solid, coherent elasticity, and may be picked up on a spatula (the equivalent non-conjugated collagen, Zyderm ® collagen implant is more fluid). The resulting material may be diluted with PBS to provide a dispersion having 20.5 mg/mL collagen-PEG.

(B) Similarly, proceeding as in part (A) above but substituting polypropylene glycol and POE-POP block polymers for polyethylene glycol, the corresponding collagen-PPG and collagen-POE-POP compositions are prepared.

(C) Difunctional PEG 3400 (34 g, 10 mmol, Aldrich Chemical Co.) is dissolved in 1,2-dichoroethane (250 mL) and heated at reflux with glutaric anhydride (10 g) and pyridine (4 mL) under nitrogen for 3 days. The solution is then filtered and the solvent evaporated, and the residue dissolved in water (100 mL) and washed with diethyl ether (2×50 mL). The resulting PEG-diglutarate is extracted from the water with chloroform (2×50 mL), and the chloroform evaporated to yield PEG-diglutarate. The PEG-diglutarate is then dissolved in DMF (200 mL) at 37° C., and N-hydroxysuccinimide (10% molar xs) added. The solution is cooled to 0° C., and an equivalent amount of dicyclohexylcarbodiimide added in DMF solution (10 mL). The mixture is left at room temperature for 24 hours, and then filtered. Cold benzene (100 mL) is then added, and the PEG-di(succinimidyl glutarate) (dPEG-SG) precipitated by adding petroleum ether (200 mL) at 0° C. The precipitate is collected on a sintered glass filter. Dissolution in benzene, followed by precipitation with petroleum ether is repeated three times to provide "activated" dPEG (dPEG*).

Vitrogen 100® collagen in solution (400 mL, 1.2 g collagen, 0.004 mmol) was mixed with 0.2M phosphate buffer (44 mL) to elevate the pH to 7.4. Next, a three-fold molar excess of dPEG* (6.00 g, 1.2 mmol) was dissolved in water for injection (40 mL) and sterile-filtered. The dPEG* solution was then added to the collagen solution, agitated, and the mixture allowed to stand at 17°-22° C. for about 15 hours. The solution was then centrifuged, and the resulting pellet of reconstituted fibrils collected and washed with PBS (3×400 mL) to remove residual dPEG*. The pellet was then placed in a syringe fitted with a Luer lock hub connected to a second syringe, and was passed between the syringes until homogeneous. The resulting material is a microgel or a particulate suspension of random size fibrils in solution (microgel conjugate). The material is a smooth, pliable, rubbery mass, with a shiny appearance.

(D) Preparation of Cartilaginoid Conjugates: Approximately 20% by weight of dPEG* (pH 7) was added to collagen in solution (33.8 mg/mL), and incubated at 21° C. for about 16 hours. The resulting conjugate was washed with 100 mL PBS 3-5 times over 12 hours. The resulting cartilaginoid non-fibrillar collagen-polymer conjugate (NFC-F cartilage) was a translucent solid with coherent elasticity. The product contained approximately 20-80% fibrillar collagen.

Another NFC cartilage composition was prepared by mixing dPEG* solution (0.6 g, pH 3) with collagen in solution (33.8 mg/mL, pH 2). The mixture was passed between two syringes joined by a Luer lock connector to form a homogenous solution. A solution of dPEG* (20% w/v) in a neutralizing buffer was then added to result in a substantially non-fibrillar collagen (NFC) cartilage material. The resulting product contained approximately 1-40% fibrillar collagen.

Alternatively, fibrillar collagen may be used instead of CIS to produce a cartilaginoid fibrillar collagen-polymer conjugate (F cartilage) having an opaque appearance and high fibrillar content. Such F cartilage is more porous and permeable than non-fibrillar collagen-polymer conjugates.

EXAMPLE 2

Characterization (A) Collagen-mPEG prepared in Example 1A was characterized and compared with Zyderm® collagen implant (ZCI), and glutaraldehyde-crosslinked fibrillar collagen (GAX).

Extrusion

This assay measured the force required to extrude the test composition through a 30 gauge needle. The results are shown in FIG. 1. As can be seen from the graph of force required (in Newtons) versus plunger travel, ZCI was extruded smoothly, requiring a force of about 20-30 Newtons. GAX was not extruded smoothly, as shown by the "spiking" exhibited in the force trace. At the plateau, GAX required about 10-15N for extrusion. In contrast, collagen-mPEG demonstrated a very low extrusion force (8-10N), with little or no spiking.

Intrusion

Intrusion is a measure of the tendency of a composition to "finger" or channel into a porous bed, rather than remaining in a compact mass. Low intrusion is preferred in augmentation of soft tissue, so that the injected implant does not diffuse through the dermis and remains in place.

A 1 mL syringe fitted with a 30 gauge needle was half-filled with silicon carbide particles (60 mesh), simulating human dermis. The upper half of the syringe was filled with 0.5 mL test composition (GAX, ZCI, or collagen-mPEG) at 35 mg/mL. The plunger was then fitted, and depressed. On depression, ZCI appeared at the needle, demonstrating intrusion through the silicon carbide bed. Syringes filled with GAX or collagen-mPEG of the invention did not pass collagen, instead releasing only buffer, demonstrating no intrudability.

Helicity

The portion of each composition exhibiting nonhelical character was measured using sensitivity to digestion with trypsin. Samples were treated with the protease trypsin, which is capable of attacking only fragmented portions of the collagen protein. The extent of hydrolysis is measured by fluorescamine assay for solubilized peptides, and the results are expressed as percentage non-helical collagen. The percentage of non-helical collagen was measured 30 minutes after the beginning of the digestion period. The results indicated that ZCI was 3-10% sensitive, GAX was 1-2% sensitive, and collagen-mPEG was about 1% sensitive. Sensitivity to trypsin may also correlate to sensitivity to endogenous proteases following implantation.

Collagenase Sensitivity

The sensitivity of each composition to collagenase was also measured. ZCI was 65.2% digested, compared to 2.2% for GAX, and 45.8% for collagen-mPEG.

Phase Transition

The behavior of each composition vs. temperature was examined using a differential scanning calorimeter. On heating, ZCI exhibited multiple peaks at about 45° and 53° C. GAX exhibited a peak at 67°-70° C. Collagen-mPEG exhibited a peak at 56°-61° C.

Lysine Content

The number of free lysines per mole was determined for each composition using TNBS to quantify reactive epsilon amino groups. ZCI exhibited about 30 lysines per (single helix) molecule (K/m), whereas GAX exhibited 26-27 K/m, and collagen-mPEG 21-26 K/m.

(B) Characterization of Crosslinked Collagen-Polymer Conjugates:

A collagen-dPEG conjugate prepared as described in Example 1C was characterized using differential scanning calorimetry (DSC). This test is a measure of the transition temperature during fragmentation of the collagen molecule at a microscopic level. A lowering of the transition temperature indicates an increase in fragmentation in a manner similar to that measured by trypsin sensitivity.

The collagen-dPEG conjugate showed a single denaturational transition at 56° C. by DSC, which is similar to the typical melting point of the Collagen-PEG conjugate prepared in Example 1A. In comparison, ZCI has a melting temperature of 45°-53° C. with multiple denaturational transitions, and GAX has a melting temperature of 67°-70° C. with a single denaturational transition.

The extrusion test described in Example 2A could not be used to characterize the collagen-dPEG conjugate because the material was not extrudable through a 30 gauge needle.

Using the intrusion test described in Example 2A, the passage of collagen-dPEG was completely blocked at the silicon carbide bed, which indicates high crosslinking between the collagen molecules and little or no intrudability.

EXAMPLE 3

Immunogenicity (A) Non-crosslinked PEG-Collagen: This experiment was conducted to demonstrate the relative immunogenicity of a collagen-mPEG preparation of the invention versus a commercially-available bovine collagen formulation prepared from essentially the same source material, and having a similar consistency. As both collagen preparations were prepared using atelopeptide collagen (which is only weakly immunogenic), the preparations were formulated with either complete Freund's adjuvant (CFA) or incomplete Freund's adjuvant (IFA), to enhance the immune response. This is a severe test, designed to magnify any possible immune reaction.

Collagen-mPEG was prepared as in Example 1A above. Male Hartley guinea pigs (11) were anesthetized and bled by heart puncture for pre-immunization serologic evaluation. Five animals were treated with two 0.1 mL intramuscular injections of Zyderm ® collagen implant (ZCI) emulsified in CFA (1:9) in the left and right thighs. Another five animals were treated in the same fashion, using collagen-PEG (35 mg/mL) emulsified in CFA. One animal was treated with collagen-PEG in IFA. At day 14 following immunization, all animals were again bled by heart puncture, and serum obtained for antibody titer determination (using ELISA). Serology was again performed at day 30.

On day 30, following collection of serum samples, each animal was challenged intradermally with both ZCI and collagen-PEG (0.1 mL of each, one on each flank). Delayed-type hypersensitivity (DTH) was quantified as a measure of cell-mediated immunity. DTH was evaluated at 24, 48, and 72 hours post-challenge by measuring the diameter of any wheal using micrometer calipers, and noting the extent of erythema and induration. Animals were then euthanized with $CO_2$, and the injection sites excised and fixed in neutral, buffered formalin for histological study.

Serological results indicated reduced immunogenicity of collagen-PEG vs. ZCI. At day 14, 80% of ZCI immunized animals exhibited "positive" antibody responses (titer ≧ 160 at day 14), whereas 0% of the collagen-PEG immunized animals exhibited positive responses. At day 30, all ZCI-immunized animals exhibited high antibody titers, whereas none of the collagen-PEG-immunized animals (C-PEG) exhibited high titers. The data are shown in Table 1.

TABLE 1

| | Immunogenicity | | |
|---|---|---|---|
| | | Antibody Titer | |
| Animal | Treatment | day 14 | day 30 |
| 1 | ZCI | 320 | >2560 |
| 2 | ZCI | 320 | 1280 |
| 3 | ZCI | 2560 | >2560 |
| 4 | ZCI | 320 | >2560 |
| 5 | ZCI | 80 | 2560 |
| 6 | C-PEG | 0 | 0 |
| 7 | C-PEG | 0 | 160 |
| 8 | C-PEG | 40 | 640 |
| 9 | C-PEG | 0 | 20 |
| 10 | C-PEG | 0 | 640 |
| 11 | C-PEG (IFA) | 0 | 160 |

Responses to the DTH challenge also demonstrated that the collagen-mPEG of the invention is less immunogenic. Guinea pigs immunized with ZCI and challenged with ZCI exhibited a wheal measuring 1,128±0,058 cm in diameter. Animals immunized with collagen-mPEG and challenged with collagen-mPEG exhibited wheals measuring 0.768±0.036 cm. Animals immunized with ZCI and challenged with collagen-mPEG, or immunized with collagen-mPEG and challenged with ZCI, developed wheals smaller than the ZCI-immunized ZCI-challenged wheals. Responses measured at 48 and 72 hours were essentially the same or lower than the 24 hour response for each site. Erythema was essentially the same for all animals.

Histological studies showed that both materials exhibited comparable intrusion, fingering into the dermis and subcutaneous space. Sites of intradermal challenge with ZCI in ZCI-immunized animals exhibited the most extensive inflammatory response, including a cellular infiltrate of lymphohistiocytic elements with eosinophils and occasional giant cells. Two of the implant sites demonstrated an erosive inflammation of the overlying epidermis and eschar formation. Sites of intradermal challenge with collagen-mPEG in ZCI-immunized animals exhibited only a moderate associated inflammatory infiltrate, with a marked reduction in acute cells and lymphoid elements. Histiocytes and giant cells were more prevalent, and in some samples lined and colonized the implants heavily. Animals immunized with collagen-mPEG exhibited only slight to moderate reaction, with ZCI challenge sites accompanied by a modest lymphohistiocytic perivascular infiltrate with a few eosinophils and giant cells. Collagen-mPEG challenge sites were typically accompanied by a minimal scattering of lymphoid cells near the associated vasculature.

(B) Crosslinked dPEG-Collagen Conjugates: Collagen-dPEG conjugates were prepared as in Example 1D. The samples were implanted in the dorsal subcutis and as cranial onlays in rats. After implantation for 30 days in the subcutis, NFC cartilage and NFC-F cartilage materials had a homogeneous microfibrillar structure. Mild colonization by connective tissue cells occurred at the periphery of the NFC-F cartilage samples, and mild capsule formation was present. No colonization had occurred with the NFC cartilage material and mild capsule formation was present. F cartilage had a very fibrous structure with mild but frequently deep colonization by connective tissue cells and sparse numbers of adipocytes. Trace amounts of capsule were present in limited areas of the F cartilage samples. NFC cartilage materials tended to retain their pre-implantation shape, with sharply defined edges, while the NFC-F cartilage samples tended to flatten over time and develop rounded profiles.

When implanted as cranial onlays, the appearance of each of the materials was similar to that in the subcutis except that the samples tended to become anchored to the skull via integration of the capsule or surrounding loose connective tissue with the periosteum.

All of the samples appeared to be biocompatible, have differing degrees of colonization by host tissues, and varying mechanical characteristics.

EXAMPLE 4

In situ Crosslinking

A dPEG solution was prepared as described in Example 1C above. The following samples were then prepared:

(1) 5 mg dPEG in 80 µL water, mixed with 0.5 mL fibrillar collagen (35 mg/mL), to a final dPEG concentration of 1% by volume;

(2) 15 mg dPEG in 80 µL water, mixed with 0.5 mL fibrillar collagen (35 mg/mL), to a final dPEG concentration of 3% by volume;

(3) Vitrogen® 100 collagen in solution;

(4) 5 mg dPEG in 80 µL water, mixed with 0.5 mL non-fibrillar collagen (35 mg/mL), to a final dPEG concentration of 1% by volume;

(5) 15 mg dPEG in 80 µL water, mixed with 0.5 mL non-fibrillar collagen (35 mg/mL), to a final dPEG concentration of 3% by volume;

(6) 5 mg dPEG in 0.5 ml PBS, to a final dPEG concentration of 1% by volume; and (7) GAX.

The dPEG solutions of Samples 1, 2, 4, and 5 were placed in a 1 mL syringe equipped with a Luer lock fitting and connector, and joined to another syringe containing the collagen material. The solutions were mixed by passing the liquids back and forth between the syringes several times to form the homogeneous reaction mixture.

The syringe connector was then removed and replaced with a 27 gauge needle, and approximately 50 µL of the reaction mixture was injected intradermally into each of 20 guinea pigs. Samples 3, 6, and 7 were similarly administered through a 27 gauge needle. At intervals up to 30 days following injection, the treatment sites were harvested and studied histologically.

By 30 days, all of the materials appeared to be biocompatible. Samples 1 and 2 displayed wide dispersion with an intermediate degree of interdigitation with dermal collagen fibers. Colonization by connective tissue cells was moderate, and a trace of round cell infiltrate with eosinophils was seen.

Samples 3, 4 and 5 were highly dispersed and finely interdigitated with dermal collagen fibers. Colonization was mild to moderate, and trace levels of round cell infiltration were seen.

Sample 6 had no detectable effects. Sample 7 occurred as large islands with moderate colonization and trace to mild levels of inflammation.

EXAMPLE 5

Coating of Implants

A collagen-dPEG reaction mixture was prepared as described in Example 1C above. A titanium implant was dipped into the reaction mixture approximately 20 minutes after crosslinking was initiated. The implant was then allowed to finish crosslinking, and dry overnight.

EXAMPLE 6

Collagen-Polymer-Growth Factor Conjugates (A) A conjugate containing crosslinked collagen-dPEG-TGF-$\beta$2 was prepared as follows: A solution of TGF-$\beta$2 and $^{125}$I-TGF-$\beta$2 ($10^5$ cpm; 25 µL of 1 mg/mL) was added to a solution of dPEG* (4 mg) in $CH_2Cl_2$ (100 µL), and the mixture allowed to react for 12 (sample #3) or 35 (sample #5) minutes at 17° C. To this was added 2.5 mL of collagen solution (3 mg/mL atelopeptide nonfibrillar collagen), and the resulting mixture allowed to incubate overnight at ambient temperature. The pellet which formed was collected by centrifugation to provide collagen-dPEG-TGF-$\beta$2.

(B) A composition based on fibrillar atelopeptide collagen was prepared as in part A above, but limiting TGF-$\beta$2/dPEG* reaction time to 2 minutes, and substituting 7 mg of fibrillar collagen (precipitated from collagen in solution within 2 minutes prior to use) for collagen in solution.

(C) A composition containing dPEG-crosslinked collagen and free TGF-$\beta$2 was prepared as follows: A solution of dPEG* (4 mg) in $CH_2Cl_2$ (100 µL), was added to 2.5 mL of CIS (3 mg/mL atelopeptide nonfibrillar collagen), and the resulting mixture allowed to incubate overnight at ambient temperature. The pellet which formed was washed to remove unreacted dPEG*, and 25 µg of TGF-$\beta$2 mixed in to provide collagen-dPEG+TGF-$\beta$2.

Figure 2:
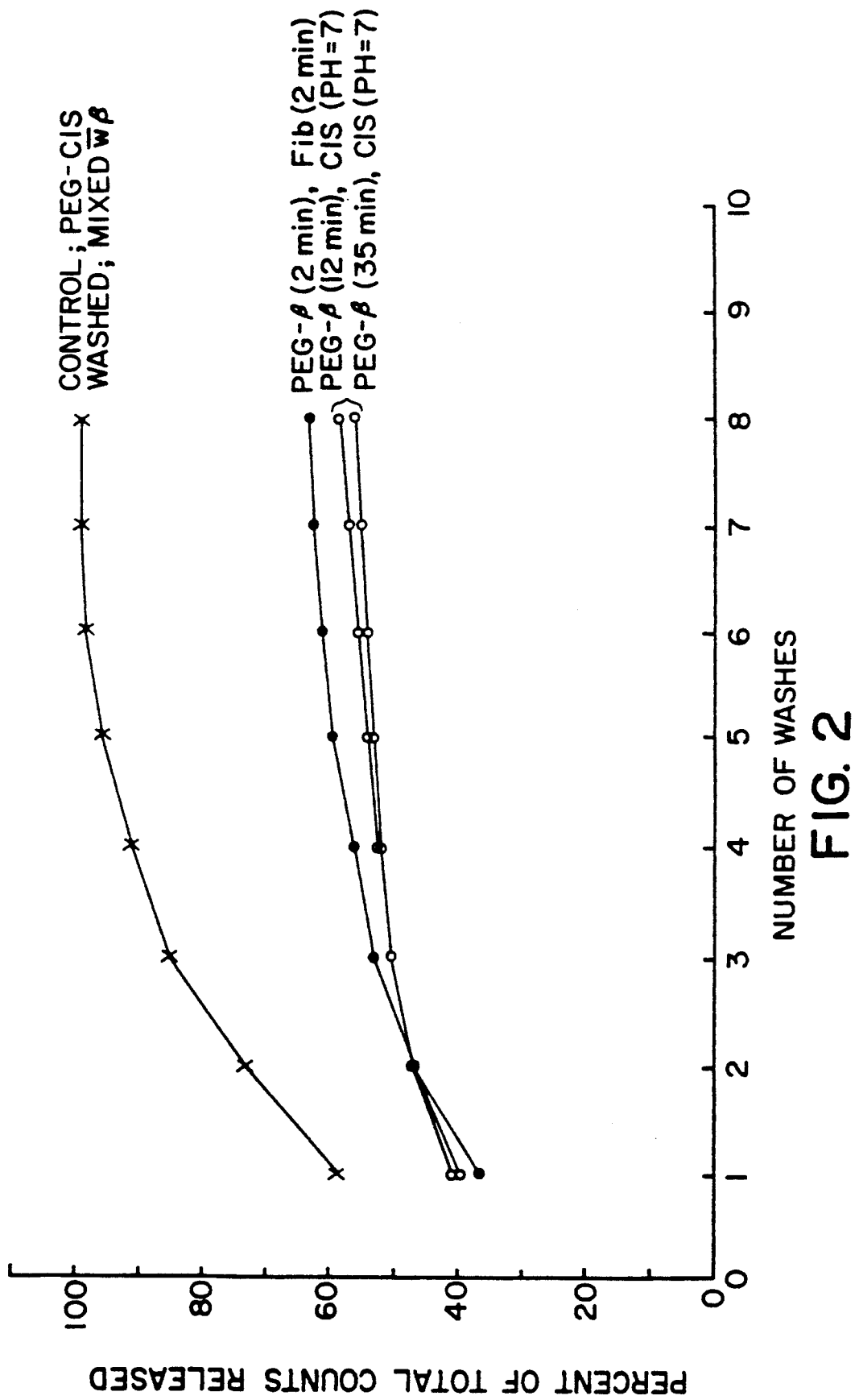
FIG. 2 illustrates the results of the experiment conducted in Example 6E, demonstrating the retention of biologically active TGF-$\beta 1$ in a crosslinked collagen-dPEG composition.

(D) The degree of TGF-$\beta$2 binding was determined as follows: Each composition prepared in parts A–C above was washed six times with 0.5 mL of buffer (0.02M phosphate buffer, 0.1% BSA) by vigorous vortexing followed by centrifugation in order to remove non-bound TGF-$\beta$2. The pellet and supernatants were collected at each time of washing, and were counted. FIG. 2 demonstrates the release rate of the compositions of part A (open circles) and part B (filled circles) versus the simple mixture prepared in part C (x's), showing the number of counts released as a function wash cycle. As shown in the figure, the TGF-$\beta$2 in the simple mixture is quantitatively released within about 6 washings, while approximately 40% of the TGF-$\beta$2 is retained in the compositions of part B and 50% is retained in the compositions of part A.

(E) The biological activity of the materials prepared above was assayed as follows: Compositions prepared according to part A (CIS-dPEG-TGF-$\beta$2) (TGF-$\beta$2/dPEG* reaction time of 12 minutes) and part C (CIS-dPEG+TGF-$\beta$2) were prepared, as well as a control prepared according to part C without TGF-$\beta$2 (CIS-dPEG). The samples were washed in PBS/BSA eight times as described in part D, then washed an additional three times in fetal bovine serum (Gibco) at 37° C. This washing protocol resulted in visually detectable material loss, so remaining TGF-β2 content was determined by counting the remaining $^{125}$I. TGF-β2 activity was then assayed by ELISA. The results are shown in Table 2 below.

TABLE 2

| Sample | Retention of Biological Activity | | |
|---|---|---|---|
| | $^{125}$I Counts | remaining TGF-β2 (μg) | O.D. (414 nm) |
| CIS-dPEG | 0 | 0 | 0.015 |
| | | | 0.015 |
| CIS-dPEG + TGF-β2 | 2775 | 0.5–1.0 | 0.029 |
| | | | 0.035 |
| CIS-dPEG-TGF-β2 | 42604 | 7.4 | 0.102 |
| | | | 0.082 |

The data demonstrates that the TGF-β1 retained in the compositions of the invention remains in a substantially active form.

EXAMPLE 7

Formulations (A) A formulation suitable for implantation by injection was prepared by suspending collagen-PEG in sterile water for injection, at 35 mg/mL. The characteristics of the resulting formulation are described in Example 2 above.

(B) A formulation useful for repair of stress-bearing bone defects (e.g., fractures, nonunions, and the like) may be prepared by mixing collagen-PEG of the invention with a suitable particulate, insoluble component. The insoluble component may be fibrillar crosslinked collagen, gelatin beads, polytetrafluoroethylene beads, silicone rubber beads, hydrogel beads, silicon carbide beads, mineral beads, or glass beads, and is preferably a calcium mineral, for example hydroxyapatite and/or tricalcium phosphate.

Solid formulations were prepared by mixing Zyderm® II (65 mg/mL collagen) or collagen-mPEG (63 mg/mL) with particulate hydroxyapatite and tricalcium phosphate (HA+TCP) and air drying to form a solid block containing 65% HA by weight. Optionally, blocks were heat-treated by heating at 75° C. for 10 hours. The resulting blocks were hydrated in 0.13M saline for 12 hours prior to testing.

On standing, it was observed that Zyderm®-HA+TCP (Z-HA) compositions separated into three phases, whereas PEG-collagen-HA+TCP (PC-HA) compositions remained single phase.

Each block was elongated by 5%, and its stress relaxation monitored for 1 minute after release. After this test, each block was subjected to constant elongation at a constant 1 cm/min until failure. The results are shown in Table 3:

TABLE 3

| | Mechanical Strength | | | | |
|---|---|---|---|---|---|
| | Stress Relaxation | | | Constant Extension | |
| Sample | Peak Force | Constant Force | t½ (min) | Rupture Force | Extension at Rupture |
| Z-HA | 1.5 | 1.1 | 0.04 | 2.6 | 11.0% |
| (air) | — | — | — | 2.6 | 15.3% |
| Z-HA | 1.5 | 1.1 | 0.06 | — | — |
| (heat) | 1.4 | 1.0 | 0.07 | 3.4 | 14.0% |
| PC-HA | 2.6 | 1.8 | 0.06 | 5.5 | 12.3% |
| (air) | 2.8 | 2.1 | 0.08 | 5.4 | 11.7% |
| PC-HA | 3.3 | 2.6 | 0.04 | 5.4 | 12.0% |
| (heat) | 3.6 | 2.7 | 0.06 | 5.4 | 20.3% |

All forces reported in newtons. Extension at rupture (strain) reported in percent extension.

The data demonstrate that collagen-polymer forms HA+TCP compositions exhibiting substantially greater tensile strength. Thus, one can prepare implant compositions with collagen-polymer which are substantially stronger than compositions employing the same amount of non-conjugated collagen, or may reduce the amount of collagen-polymer employed to form a composition of equal strength.

The instant invention is shown and described herein at what is considered to be the most practical, and preferred embodiments. It is recognized, however, that departures may be made therefrom which are within the scope of the invention and that obvious modifications will occur to one skilled in the art upon reading this disclosure.

What is claimed:

1. A conjugate comprising collagen chemically conjugated by an ether bond to a synthetic nonimmunogenic hydrophilic polymer.

2. The conjugate of claim 1, wherein the synthetic hydrophilic polymer is a difunctional activated polyethylene glycol.

3. The conjugate of claim 2, wherein the polymer is monomethylated polyethylene glycol activated at each end.

4. The conjugate of claim 1, wherein the conjugate has the following general structural formula:

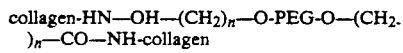

collagen-HN—OH—(CH$_2$)$_n$—O-PEG-O—(CH$_2$-)$_n$—CO—NH-collagen wherein n is an integer selected from the group consisting of 0, 1, 2, 3, or 4.

5. The composition of claim 1, wherein the collagen is selected from the group consisting of type I, type II and type III collagen and the polymer is polyethylene glycol having a weight average molecular weight of about 100 to about 20,000.

6. The composition of claim 5 wherein said synthetic hydrophilic polymer is bound to an available lysine residue on said collagen.

7. The composition of claim 6 wherein the ratio of collagen molecules to polymer molecules is in the range of about 1:1 to about 1:20.

8. The composition of claim 6 wherein said atelopeptide collagen is fibrillar collagen.

9. The conjugate of claim 1, wherein the collagen is atelopeptide collagen and further comprising:
a therapeutically effective amount of a cytokine.

10. The conjugate of claim 9 wherein the cytokine is selected from the group consisting of epidermal growth factor, transforming growth factor-α, transforming growth factor-β, transforming growth factor-β2, platelet-derived growth factor-AA, platelet-derived growth factor-AB, platelet-derived growth factor-BB, acidic fibroblast growth factor, basic fibroblast growth factor, connective tissue activating peptide, β-thromboglobulin, insulin-like growth factors, tumor necrosis factor, interleukine, colony stimulating factors, erythropoietin, nerve growth factor, interferons, and osteogenic factors.

11. The conjugate of claim 10, wherein the cytokine is selected from the group consisting of transforming growth factor-β, transforming growth factor-β1, transforming growth factor-β2, and erythropoietin.

12. The conjugate of claim 1, wherein the synthetic hydrophilic polymer is a succinimidyl monomethyl-polyethylene glycol glutarate.

13. The conjugate of claim 1, wherein the collagen is atelopeptide collagen and further comprising:
a sufficient amount of a fluid pharmaceutically acceptable carrier to render the composition containing the conjugate flowable and injectable.

14. The conjugate of claim 1, wherein the polymer is monomethyl-polyethylene glycol having a weight average molecular weight of about 1,900 to about 8,000.

15. The conjugate of claim 1, wherein the synthetic hydrophilic non-immunogenic polymer has the following structural formula:

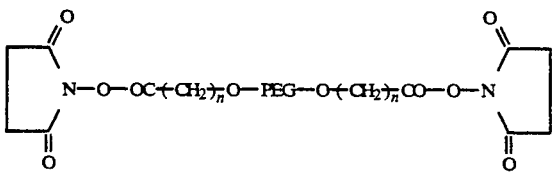

wherein n is selected from the group consisting of 0, 1, 2, 3 and 4.

16. The conjugate of claim 1, wherein the synthetic, hydrophilic, non-immunogenic polymer has the following structural formula:

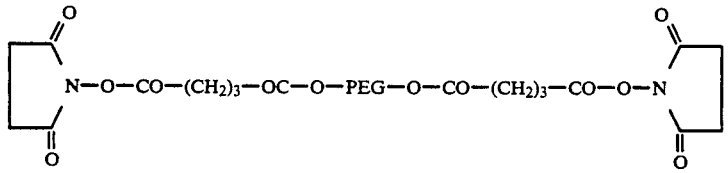

17. The conjugate of claim 1, wherein the synthetic, hydrophilic, non-immunogenic polymer has the following structural formula:

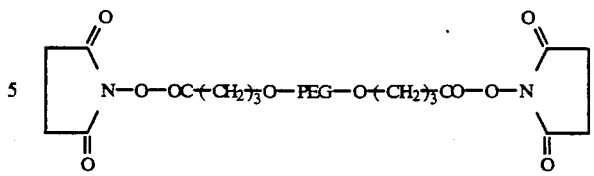

18. The conjugate of claim 1, wherein the synthetic, hydrophilic, non-immunogenic polymer has the following structural formula:

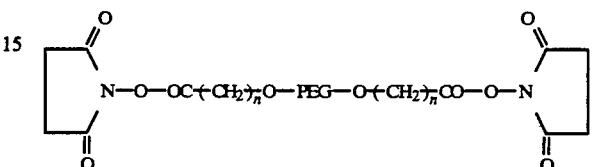

wherein n is selected from the group consisting of 0, 1, 2, 3 and 4.

19. The conjugate of claim 1 wherein said composition comprises about 10 to about 100 mg/mL collagen and about 0.1 to about 30% synthetic hydrophilic polymer having reactive groups.

20. The conjugate of claim 19, wherein said composition comprises about 30 to about 80 mg/mL collagen and about 0.3 to about 10% synthetic hydrophilic polymer having reactive groups.

21. The conjugate of claim 1 wherein the collagen comprises fibrillar collagen.

22. The conjugate of claim 1 wherein the collagen comprises non-fibrillar collagen.

23. The conjugate of claim 1 further comprising a suitable particulate material selected from the group consisting of fibrillar, crosslinked collagen, gelatin beads, polytetrafluoroethylene beads, silicone rubber beads, hydrogel beads, silicon carbide beads, glass beads, calcium carbonate particles, hydroxyapatite particles, tricalcium phosphate particles, or mixtures of hydroxyapatite and tricalcium phosphate particles.

24. The conjugate of claim 1, further comprising a particulate material selected from the group consisting of hydroxyapatite particles, tricalcium phosphate particles, or mixtures of hydroxyapatite and tricalcium phosphate particles having an average diameter of about 1 to 20 microns in diameter.

25. The conjugate as claimed in claim 1, wherein the collagen is atelopeptide collagen.

* * * * *